United States Patent
Gothelf et al.

(10) Patent No.: US 10,564,149 B2
(45) Date of Patent: Feb. 18, 2020

(54) POPULATIONS OF MESENCHYMAL STEM CELLS THAT SECRETE NEUROTROPHIC FACTORS

(71) Applicant: BrainStorm Cell Therapeutics Ltd., Petach-Tikva (IL)

(72) Inventors: Yael Gothelf, Kiryat-Ono (IL); Yosef Levy, Modiin (IL)

(73) Assignee: BrainStorm Cell Therapeutics Ltd., Petach-Tikva (IL)

( * ) Notice: Subject to any disclaimer, the term of this patent is extended or adjusted under 35 U.S.C. 154(b) by 0 days.

(21) Appl. No.: 15/113,105

(22) PCT Filed: Feb. 11, 2015

(86) PCT No.: PCT/IL2015/050159
§ 371 (c)(1),
(2) Date: Jul. 21, 2016

(87) PCT Pub. No.: WO2015/121859
PCT Pub. Date: Aug. 20, 2015

(65) Prior Publication Data
US 2016/0334392 A1 Nov. 17, 2016

Related U.S. Application Data

(60) Provisional application No. 61/938,172, filed on Feb. 11, 2014.

(51) Int. Cl.
*A61K 35/28* (2015.01)
*G01N 33/50* (2006.01)
*C12N 5/0775* (2010.01)

(52) U.S. Cl.
CPC ......... *G01N 33/5073* (2013.01); *A61K 35/28* (2013.01); *C12N 5/0663* (2013.01); *C12N 2501/115* (2013.01); *C12N 2501/135* (2013.01); *C12N 2501/195* (2013.01)

(58) Field of Classification Search
None
See application file for complete search history.

(56) References Cited

U.S. PATENT DOCUMENTS

| | | | |
|---|---|---|---|
| 2010/0184033 A1 | 7/2010 | West et al. | |
| 2012/0009673 A1 | 1/2012 | Kadouri et al. | |
| 2014/0234276 A1* | 8/2014 | Germann | A61K 9/0019 424/93.21 |
| 2015/0209389 A1 | 7/2015 | Gothelf et al. | |
| 2018/0296607 A1 | 10/2018 | Gothelf et al. | |

FOREIGN PATENT DOCUMENTS

| | | |
|---|---|---|
| DE | 102011121982 * | 4/2013 |
| EP | 1479767 | 11/2004 |
| EP | 2285951 | 2/2011 |
| JP | 2003-144155 | 5/2003 |
| WO | WO 2004/046348 | 6/2004 |
| WO | WO 2006/134602 | 12/2006 |
| WO | WO 2007/066338 | 6/2007 |
| WO | WO 2009/144718 | 12/2009 |
| WO | WO 2011/063005 | 5/2011 |
| WO | WO 2014/024183 | 2/2014 |
| WO | WO 2015/121859 | 8/2015 |

OTHER PUBLICATIONS

Cho et al Transplantation of mesenchymal stem cells enhances axonal outgrowth and cell survival in an organotypic spinal cord slice culture Neuroscience Letters 454 (2009) 43-48.*
Communication Pursuant to Article 94(3) EPC dated May 24, 2017 From the European Patent Office Re. Application No. 13767124.4. (4 Pages).
Office Action dated Jun. 29, 2017 From the Israel Patent Office Re. Application No. 237124 and Its Translation Into English. (4 Pages).
Official Action dated May 31, 2017 From the US Patent and Trademark Office Re. U.S. Appl. No. 14/419,668. (19 pages).
Corning "Dulbecco's Modification of Eagle's Medium (DMEM) Formulation," Mediatech, Inc., a Corning Subsidiary, New York, 2012.
Movaghar et al. "Transdifferentiation of Bone Marrow Stromal Cells into Schwann Cell Phenotype Using Progesterone as Inducer," Brain Research 1208: 17-24, 2008.
Communication Pursuant to Article 94(3) EPC dated Jun. 13, 2016 From the European Patent Office Re. Application No. 13767124.4.
International Preliminary Report on Patentability dated Feb. 19, 2015 From the International Bureau of WIPO Re. Application No. PCT/IL2013/050660.
International Preliminary Report on Patentability dated Aug. 25, 2015 From the International Bureau of WIPO Re. Application No. PCT/IL2015/050159.
International Search Report and the Written Opinion dated Jun. 15, 2015 From the International Searching Authority Re. Application No. PCT/IL2015/050159.
International Search Report and the Written Opinion dated Nov. 22, 2013 From the International Searching Authority Re. Application No. PCT/IL2013/050660.
Office Action dated Apr. 14, 2016 From the Israel Patent Office Re. Application No. 237124 and Its Translation Into English.

(Continued)

*Primary Examiner* — Maria G Leavitt

(57) ABSTRACT

A method of qualifying whether a cell population is a suitable therapeutic is disclosed. The method comprises:
(a) incubating a population of undifferentiated mesenchymal stem cells (MSCs) in a differentiating medium comprising basic fibroblast growth factor (bFGF), platelet derived growth factor (PDGF), heregulin and cAMP for at least two days to obtain a population of differentiated MSCs; and
(b) analyzing the expression of CD49 a in the differentiated MSC population, wherein an amount of CD49 a above a predetermined level indicative of the cell population being suitable as a therapeutic.

5 Claims, 4 Drawing Sheets
(3 of 4 Drawing Sheet(s) Filed in Color)

(56) References Cited

OTHER PUBLICATIONS

Figure 1:
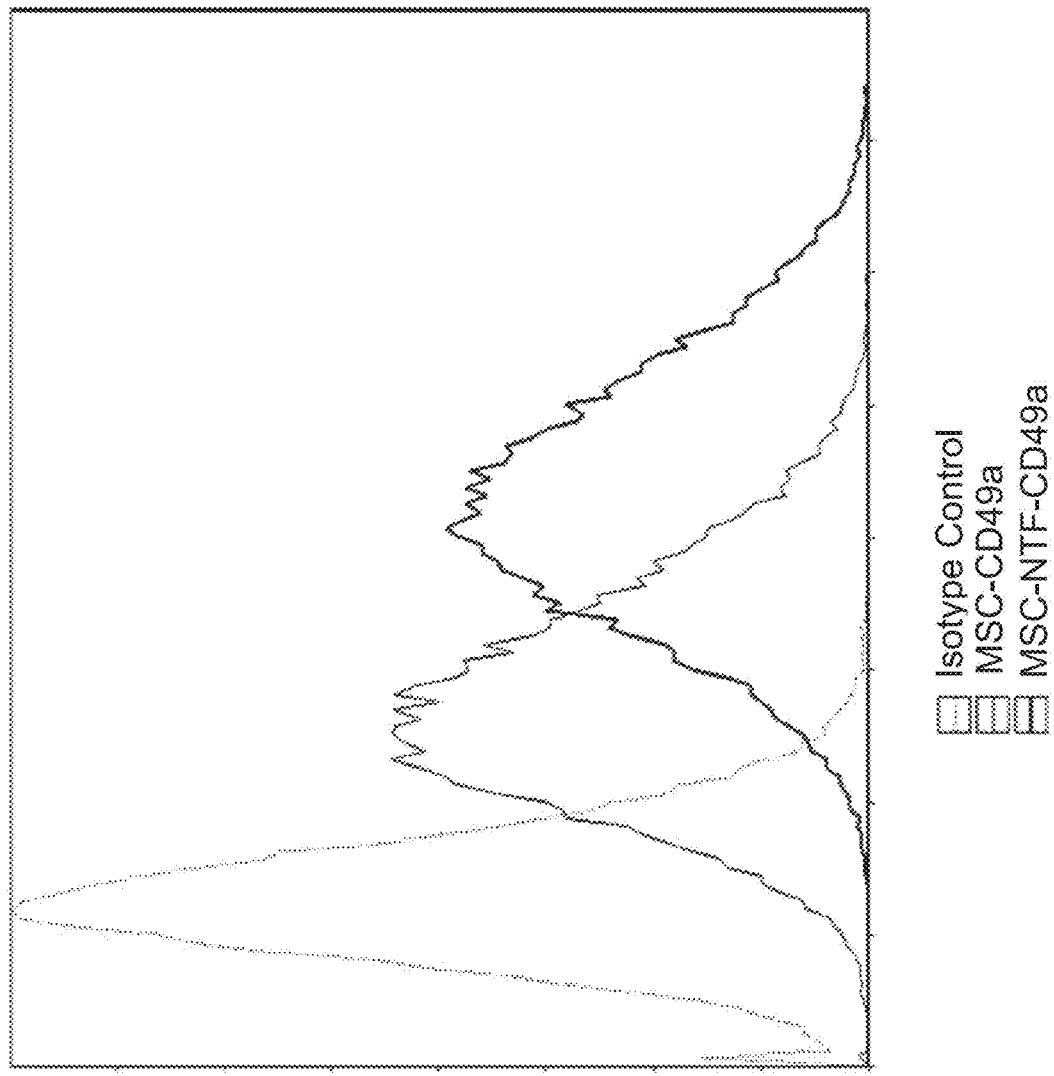

Official Action dated Oct. 4, 2016 From the US Patent and Trademark Office Re. U.S. Appl. No. 14/419,668.
Official Action dated Apr. 22, 2016 From the US Patent and Trademark Office Re. U.S. Appl. No. 14/419,668.
Restriction Official Action dated Jan. 25, 2016 From the US Patent and Trademark Office Re. U.S. Appl. No. 14/419,668.
Abbaszadeh et al., "Bone Marrow Stromal Cell Transdifferentiation into Oligodendrocyte-Like Cells Using Triiodothyronine as a Inducer with Expression of Platelet-Derived Growth Factor Alpha as a Maturity Marker," Iranian Biomedical Journal 17(2):62-70, Apr. 2013.
Bossolasco et al. "Neuro-Glial Differentiation of Human Bone Marrow Stem Cells In Vitro", Experimental Neurology, XP004875161, 193(2): 312-325, Jun. 1, 2005.
Choudhery et al. "Comparison of Human Mesenchymal Stem Cells Derived From Adipose and Cord Tissue", Cytotherapy, XP002716010, 15(3): 330-343, Mar. 2013. Fig.2.
Dezawa et al. "Specific Induction of Neuronal Cells From Bone Marrow Stromal Cells and Application for Autologous Transplantation", The Journal of Clinical Investigation, XP002311058, 113(12): 1701-1710, Jun. 1, 2004.
Garcia et al. "Bone Marrow Stromal Cells Produce Nerve Growth Factor and Glial Cell Line-Derived Neurotrophic Factors", Biochemical and Biophysical Research Communications, XP004495951, 316(3): 753-754, Apr. 9, 2004. Fig 1.
Kaka et al. "In Vitro Differentiation of Bone Marrow Stromal Cells Into Oligodendrocyte-Like Cells Using Triiodothyronine as Inducer", International Journal of Neuroscience, XP008165743, 122(5): 237-247, May 1, 2012. Table 1.
Kaka et al. "In Vitro Differentiation of Bone Marrow Stromal Cells into Oligodendrocyte-Like Cells Using Triiodothyronine as Inducer",The International Journal of Neuroscience, XP008165743, 122 (5):237-247, May 1, 2012. Abstract, Fig. 7, Table 1.
Kohyama et al. "Brain From Bone: Efficient 'Mcta-Differentiation' of Marrow Stroma-Derived Mature Osteoblasts to Neurons With Noggin or A Demethylating Agent", Differentiation, XP002974601, 68(4-5): 235-244, Oct. 1, 2001. P. 237, r-h Col., Para. 2.
Kurozumi et al. "BDNF Gene-Modified Mesenchymal Stem Cells Promote Functional Recovery and Reduce Infarct Size in the Rat Middle Cerebral Artery Occlusion Model", Molecular Therapy, XP009117446, 9(2): 189-197, Feb. 1, 2004.
Lakshmipathy et al. "Concise Review: MicroRNA Expression in Multipotent Mesenchymal Stromal Cells", Stem Cells, XP055077003, 26(2): 356-363, Feb. 1, 2008.
Matsuse et al. "Human Umbilical Cord-Derived Mesenchymal Stromal Cells Differentiate Into Functional Schwann Cells That Sustain Peripheral Nerve Regeneration", Journal of Neuropathology and Experimental Neurology, 69(9): 973-985, Sep. 2010.
Rollins et al. "Increase in Endogenous and Exogenous Cyclic AMP Levels Inhibits Sclerotial Development in Sclerotinia Sclerotiorum", Applied and Environmental Microbiology, 64(7): 2539-2544, Jul. 1998.
Official Action dated Sep. 15, 2017 From the US Patent and Trademark Office Re. U.S. Appl. No. 14/419,668. (17 pages).
Applicant-Initiated Interview Summary dated Nov. 16, 2017 From the US Patent and Trademark Office Re. U.S. Appl. No. 14/419,668. (3 pages).
Decision of Rejection dated Jan. 5, 2018 From the Japan Patent Office Re. Application No. 2015-526006 and Its Translation Into English. (12 Pages).
Park et al. "Human Mesenchymal Stem Cell-Derived Schwann Cell-Like Cells Exhibit Neurotrophic Effects, Via Distinct Growth Factor Production, in a Model of Spinal Cord Injury", Glia, 58(9): 1118-1132, Published Online Mar. 29, 2010.
Notice of Reason for Rejection dated May 23, 2017 From the Japan Patent Office Re. Application No. 2015-526006 and Its Translation Into English. (9 Pages).
Halfon et al. "Markers Distinguishing Mesenchymal Stem Cells From Fibroblasts Are Downregulated With Passaging", Stem Cells and Development, 20(1): 53-66, Dec. 2011.
Communication Pursuant to Article 94(3) EPC dated Mar. 13, 2018 From the European Patent Office Re. Application No. 13767124.4. (3 Pages).
Requisition by the Examiner dated Sep. 11, 2018 From the Innovation, Science and Economic Development Canada, Canadian Intellectual Property Office Re. Application No. 2,877,223. (3 Pages).
Translation Dated Sep. 27, 2018 of Notice of Reasons for Rejection dated Sep. 11, 2018 From the Japan Patent Office Re. Application No. 2016-548691. (8 Pages).
Office Action dated Apr. 11, 2019 From the Israel Patent Office Re. Application No. 246943 and Its Translation Into English. (6 Pages).
Office Action dated Nov. 14, 2018 From the Israel Patent Office Re. Application No. 261441 and Its Translation Into English. (6 Pages).
Communication Pursuant to Article 94(3) EPC dated Feb. 20, 2019 From the European Patent Office Re. Application No. 13767124.4. (4 Pages).
Notice of Reasons for Rejection dated Apr. 2, 2019 From the Japan Patent Office Re. Application No. 2018-81151 and Its Translation Into English. (12 Pages).
Notice of Reasons for Rejection dated Apr. 16, 2019 From the Japan Patent Office Re. Application No. 2016-548691 and Its Translation Into English. (5 Pages).

\* cited by examiner

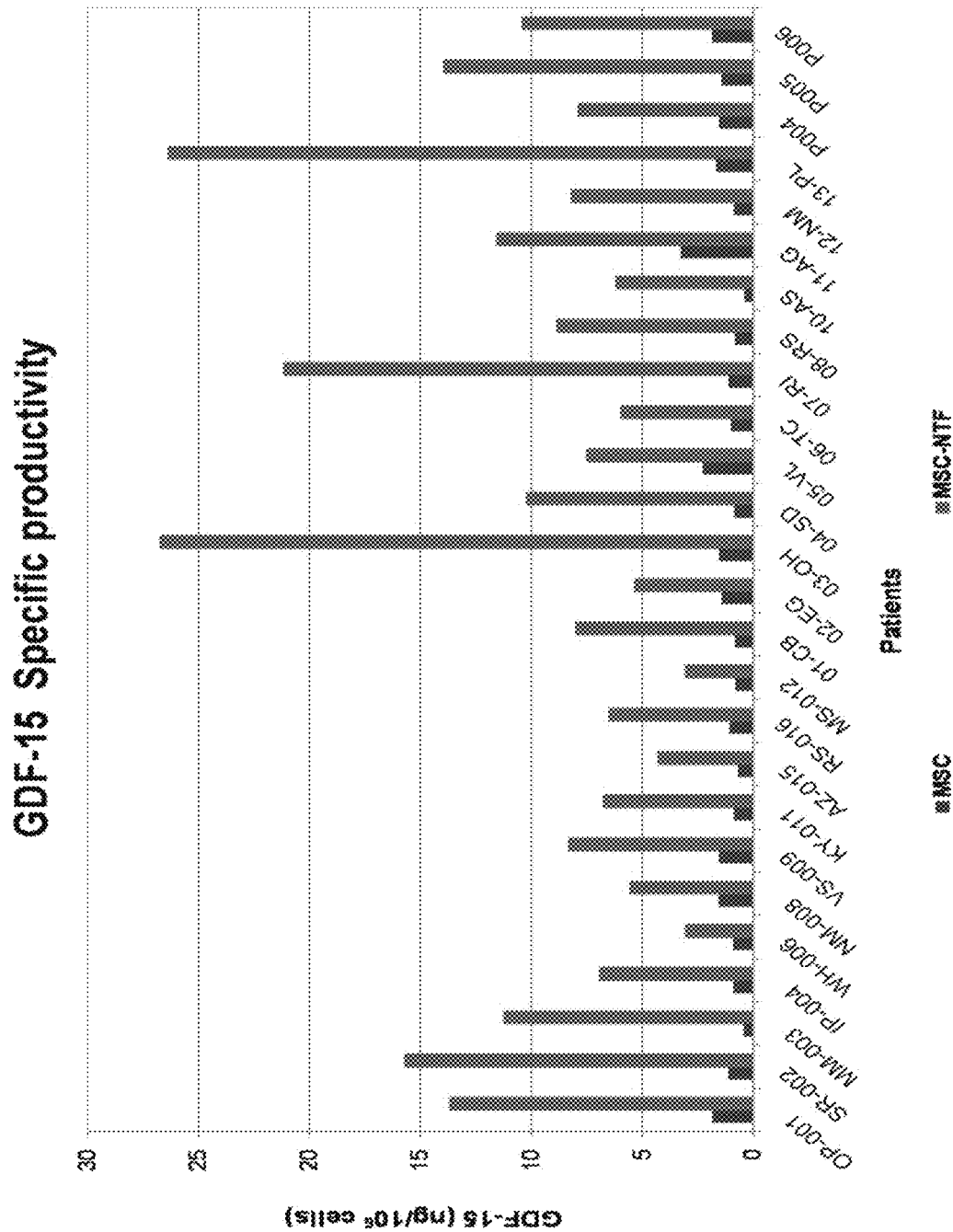

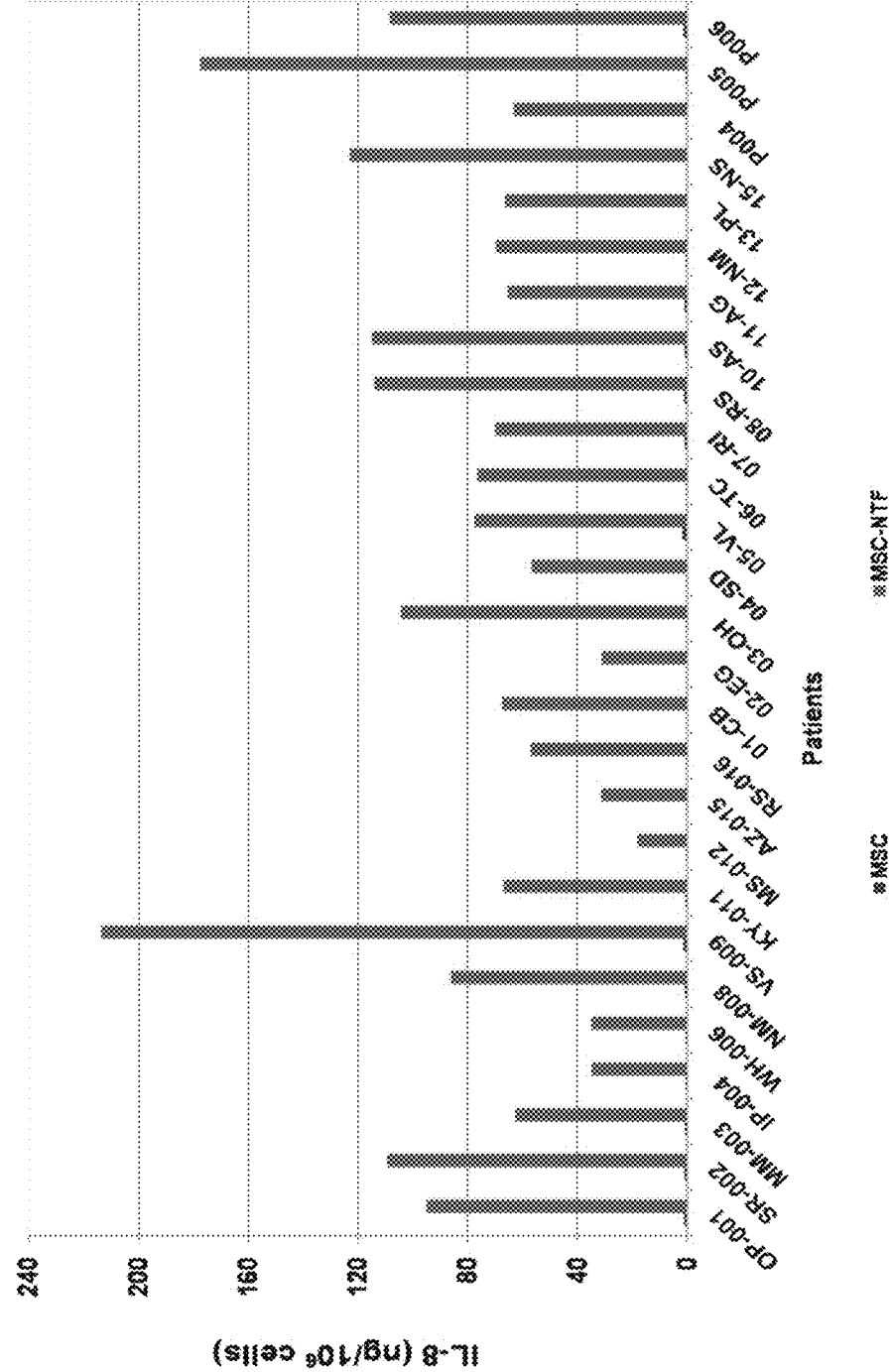

POPULATIONS OF MESENCHYMAL STEM CELLS THAT SECRETE NEUROTROPHIC FACTORS

RELATED APPLICATIONS

This application is a National Phase of PCT Patent Application No. PCT/IL2015/050159 having International filing date of Feb. 11, 2015 which claims the benefit of priority under 35 USC § 119(e) of U.S. Provisional Patent Application No. 61/938,172 filed on Feb. 11, 2014. The contents of the above applications are all incorporated by reference as if fully set forth herein in their entirety.

FIELD AND BACKGROUND OF THE INVENTION

The present invention, in some embodiments thereof, relates to a method of qualifying neurotrophic factor secreting cells based on cell surface marker expression.

Amyotrophic lateral sclerosis (ALS) is one of the most common neurodegenerative diseases in adults. It is a fatal progressive neurodegenerative disease characterized by motor-neuron cell death in the brain and spinal cord accompanied by rapid loss of muscle function and eventual complete paralysis.

Current experimental ALS drugs are developed on the basis of putative pathophysiologic mechanisms, such as anti-glutamatergic agents, drugs targeting protein misfolding and accumulation, antioxidant therapy, immunomodulatory agents, and stem cells.

Of the current investigational therapies, stem cell transplantation may have the most potential. Apart from the replacement of lost or damaged motor neurons, stem cell implantation therapy may benefit ALS patients by an independent effect of cytoprotection. Further, there is the potential for stem cells to differentiate into supportive interstitial cells including astrocytes and microglia which can potentially produce neurotrophic factors as well as enzymatic and paracrine mediators which antagonize neurotoxicity. Further experimental data have shown that non-neuronal cell replacement can be a strategic therapy in promoting motor neuron survival and improved neuromuscular function (Corti S et al. Brain (2010) 133 (2): 465-481).

The use of stem cells as a cellular source in cell replacement therapy for additional neurodegenerative diseases including Parkinson's disease and multiple sclerosis has also been suggested.

Neurotrophic factors (NTF) are small, naturally occurring polypeptides that support the development and survival of neurons, and therefore have been considered in the past few years as candidates for therapy options for different neurodegenerative diseases including ALS. Studies in ALS animal models have shown a delay in disease onset and/or progression after administration of various neurotrophic factors.

However, clinical trials of systematic or intrathecal administration of recombinant growth factors to ALS patients have not been effective, probably due in part to their short half-life, low concentrations at target sites, and high incidence of side effects.

Several studies have shown that mesenchymal stem cells (MSCs) following exposure to different factors in vitro, change their phenotype and demonstrate neuronal and glial markers [Kopen, G. C., et al., Proc Natl Acad USA. 96(19): 10711-6, 1999; Sanchez-Ramos, et al. Exp Neurol. 164(2): 247-56. 2000; Woodbury, D., J Neurosci Res. 61(4):364-70, 2000; Woodbury, D., et al., J Neurosci Res. 69(6):908-17, 2002; Black, I. B., Woodbury, D. Blood Cells Mol Dis. 27(3):632-6, 2001; Kohyama, J., et al. Differentiation. 68(4-5):235-44, 2001; Levy, Y. S. J Mol Neurosci. 21(2):121-32, 2003, Blondheim N. R., Stem Cells & Dev. 15:141-164, 2006].

WO2006/134602 and WO2009/144718 teaches differentiation protocols for the generation of neurotrophic factor secreting cells from mesenchymal stem cells.

WO2007/066338 teaches differentiation protocols for the generation of oligodendrocyte-like cells from mesenchymal stem cells.

WO2004/046348 teaches differentiation protocols for the generation of neuronal-like cells from mesenchymal stem cells.

WO 2014/024183 teaches additional differentiation protocols for the generation of cells which secrete neurotrophic factors.

SUMMARY OF THE INVENTION

According to an aspect of some embodiments of the present invention there is provided a method of qualifying whether a cell population is a suitable therapeutic comprising:

(a) incubating a population of undifferentiated mesenchymal stem cells (MSCs) in a differentiating medium comprising basic fibroblast growth factor (bFGF), platelet derived growth factor (PDGF), heregulin and cAMP for at least two days to obtain a population of differentiated MSCs; and (b) analyzing the expression of CD49a in the differentiated MSC population, wherein an amount of CD49a above a predetermined level indicative of the cell population being suitable as a therapeutic.

According to an aspect of some embodiments of the present invention there is provided an isolated population of mesenchymal stem cells having been ex vivo differentiated into cells that secrete neurotrophic factors by incubation in a differentiating medium comprising basic fibroblast growth factor (bFGF), platelet derived growth factor (PDGF), heregulin and cAMP for at least two days to obtain a population of differentiated MSCs, wherein at least 80% of the cells of the population express CD49a.

According to an aspect of some embodiments of the present invention there is provided a method of treating an immune or inflammatory related disease in a subject in need thereof, comprising administering to the subject a therapeutically effective amount of mesenchymal stem cells having been ex vivo differentiated into cells that secrete neurotrophic factors, wherein the immune or inflammatory related disease is not a neurodegenerative disease or myasthenia gravis, thereby treating the disease.

According to an aspect of some embodiments of the present invention there is provided a use of mesenchymal stem cells which have been ex vivo differentiated into cells that secrete neurotrophic factors for the treatment of an immune or inflammatory related disease, wherein the immune or inflammatory related disease is not a neurodegenerative disease or myasthenia gravis, thereby treating the disease.

According to some embodiments of the invention, the analyzing the expression of CD49a comprises analyzing the number of cells of the differentiated MSC population which express CD49a, wherein a number of cells being greater than 80% is indicative of the cell population being suitable as a therapeutic.

According to some embodiments of the invention, analyzing the expression of CD49a comprises analyzing the level of expression of CD49a in said differentiated MSC population, wherein an increase in the level of expression by more than 2 fold compared to the CD49 expression in an undifferentiated MSC population is indicative of the cell population being suitable as a therapeutic, wherein said differentiated MSC population and said undifferentiated MSC population are derived from the same donor.

According to some embodiments of the invention, the MSCs are derived from the bone marrow.

According to some embodiments of the invention, more than 95% of the cells of said population of undifferentiated MSCs express CD73, CD90 and CD105.

According to some embodiments of the invention, the populations of undifferentiated MSCs do not express CD3, CD14, CD19, CD34, CD45, and HLA-DR as determined by flow cytometry.

According to some embodiments of the invention, the incubating is effected for no more than 6 days.

According to some embodiments of the invention, the number of cells in the cell population is at least $1 \times 10^6$ cells.

According to some embodiments of the invention, the number of cells being greater than 85% is indicative of the cell population being suitable as a therapeutic.

According to some embodiments of the invention, the method further comprises determining the amount of neurotrophic factor secreted from the cells, wherein an amount of said neurotrophic factor being above a predetermined level is further indicative of the cell population being suitable as a therapeutic.

According to some embodiments of the invention, the neurotrophic factor is GDNF.

According to some embodiments of the invention, the neurotrophic factor is selected from the group consisting of GDNF, VEGF and HGF.

According to some embodiments of the invention, the predetermined level is at least 5 times greater than the amount of GDNF secreted from a non-differentiated mesenchymal stem cell obtained from the same donor.

According to some embodiments of the invention, the differentiating medium is devoid of a phosphodiesterase inhibitor.

According to some embodiments of the invention, the differentiating medium is devoid of triiodothyronine.

According to some embodiments of the invention, the phosphodiesterase inhibitor comprises IBMX.

According to some embodiments of the invention, the differentiating medium is devoid of xeno derived components.

According to some embodiments of the invention, the differentiating medium is devoid of antibiotics.

According to some embodiments of the invention, the method further comprises culturing said population of undifferentiated MSCs prior to said incubating, wherein said culturing is effected under conditions that do not promote cell differentiation.

According to some embodiments of the invention, the culturing is effected for three days following seeding of said undifferentiated MSCs.

According to some embodiments of the invention, the seeding is effected at a density of about 6000-8000 cm$^2$.

According to some embodiments of the invention, the culturing is effected in a culture medium comprising platelet lysate.

According to some embodiments of the invention, the percentage of said platelet lysate in said culture medium is about 10%.

According to some embodiments of the invention, the culture medium further comprises L-glutamine, sodium pyruvate and heparin.

According to some embodiments of the invention, the analyzing is effected by flow cytometry.

According to some embodiments of the invention, at least 90% of the cells of the population express CD49a.

According to some embodiments of the invention, at least 80% of the cells of the population express CD49a.

According to some embodiments of the invention, the cells have been ex vivo differentiated by incubation in a differentiating medium comprising basic fibroblast growth factor (bFGF), platelet derived growth factor (PDGF), heregulin and cAMP.

According to some embodiments of the invention, at least 90% of the cells of the population express CD49a.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a representative flow cytometric analysis of CD49a expression on the surface of MSC (black) and MSC-NTF (heavy black) cells of the same donor at the end of differentiation. The dotted line to the left is the isotype control (MFI of the isotype control is 0.395, of MSC 2.83 and of MSC-NTF 13.5).

FIGS. 2A-B are graphs illustrating the amount of GDF-15 (FIG. 2A) and IL-8 (FIG. 2B) in ALS patient-derived bone marrow MSCs prior to and following differentiation.

Figure 3A:
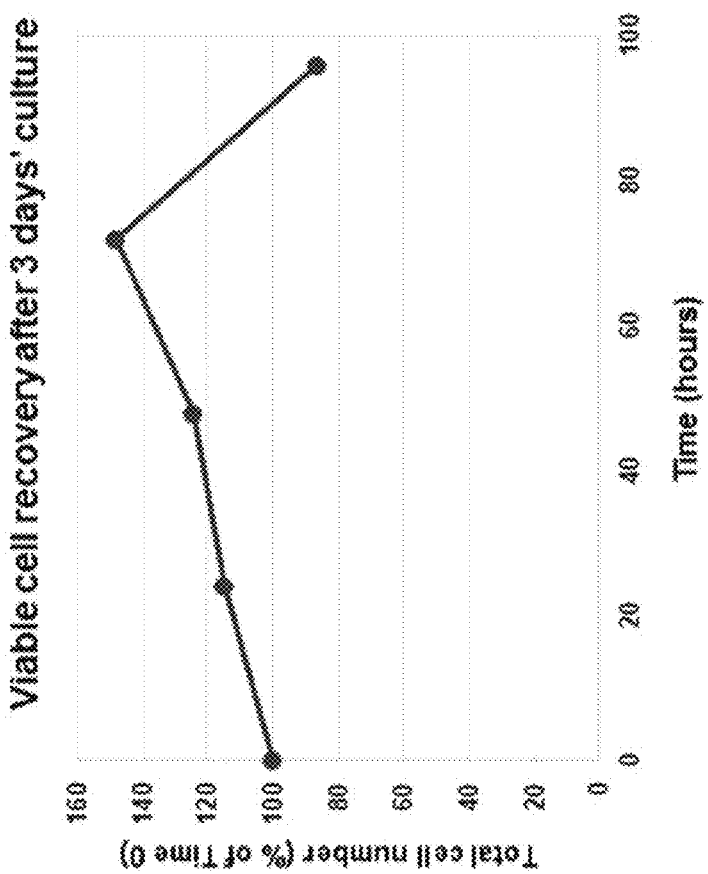
Figure 3B:
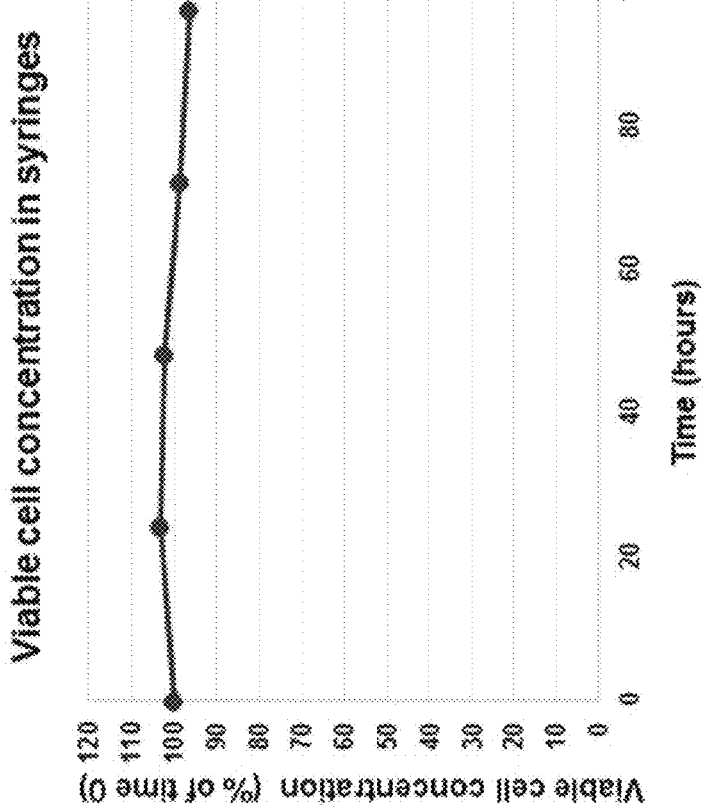

FIGS. 3A-B are graphs illustrating the stability of the cells in storage medium. Cells were incubated in syringes at 2-8° C. At 24, 48, 72 and 96 hours the cells were sampled and recovery of viable cells and viability were evaluated at each time point (FIG. 3A). At each time point, cells were also seeded in culture medium for 3 days. The recovery of viable cells and viability were evaluated at the end of each of the 3 days' culture period (calculated as the % recovery of cells seeded at time 0; FIG. 3B). Results are presented as average of 2 experiments.

DESCRIPTION OF SPECIFIC EMBODIMENTS OF THE INVENTION

The present invention, in some embodiments thereof, relates to a method of qualifying neurotrophic factor secreting cells based on cell surface marker expression.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Neurotrophic factors (NTFs) are secreted proteins that regulate the survival, functional maintenance and phenotypic development of neuronal cells. Alterations in NTF levels are involved in triggering programmed cell-death in neurons and thus contribute to the pathogenesis of Parkinson's disease and other neurodegenerative diseases.

However, the direct use of neurotrophic factors is not applicable as they do not pass the blood-brain barrier and do not distribute properly following systemic injection. Therefore, other strategies must be developed in order to take advantage of their therapeutic properties.

Protocols for differentiating human mesenchymal stem cells (MSCs) into neurotrophic factor secreting cells are known in the art—see for example WO 2006/134602 and WO 2009/144718.

The present inventors have previously developed a new one step differentiation protocol which enhances the secretion of neurotrophic factors from MSCs. The level of secretion of glial derived growth factor (GDNF) and brain derived neurotrophic factor (BDNF) was shown to be consistently up-regulated following the differentiation process, with GDNF being up-regulated by as much as 20 fold and BDNF by as much as three fold as compared to the corresponding non-differentiated cell population obtained from the same donor.

The protocol involves direct differentiation of undifferentiated MSCs in a single medium comprising basic fibroblast growth factor (bFGF), platelet derived growth factor (PDGF), heregulin and cAMP.

The present inventors have now discovered a unique and simple way of selecting for mesenchymal stem cell populations which have been successfully differentiated according to this protocol based on expression of a cell surface marker. Of the myriad of potential cell surface markers expressed on these differentiated cells, the present inventors have found CD49a can be used as a single marker to substantiate successful differentiation.

As illustrated in FIG. 1, following a successful differentiation, more than 80% of the cells obtained expressed CD49a on their cell surface. In contrast, only about 65% of the cells prior to differentiation expressed CD49a on their cell surface. In addition, the present inventors showed that the level of CD49a expression on a successfully differentiated MSC was higher than the level of CD49a expression on a non-differentiated MSC.

Thus, according to one aspect of the present invention there is provided a method of qualifying whether a cell population is a suitable therapeutic comprising:

(a) incubating a population of undifferentiated mesenchymal stem cells (MSCs) in a differentiating medium comprising basic fibroblast growth factor (bFGF), platelet derived growth factor (PDGF), heregulin and cAMP for at least two days to obtain a population of differentiated MSCs; and (b) analyzing the expression of CD49a in the differentiated MSC population, wherein an amount of CD49a above a predetermined level indicative of the cell population being suitable as a therapeutic.

As used herein, the phrase "suitable therapeutic" refers to the suitability of the cell population for treating neurodegenerative diseases and immune diseases (e.g. autoimmune diseases). According to a particular embodiment, cells which are suitable therapeutics are those that secrete sufficient neurotrophic factors that they are capable of having a therapeutic effect for a particular disease.

The term "neurodegenerative disease" is used herein to describe a disease which is caused by damage to the central nervous system. Exemplary neurodegenerative diseases which may be treated using the cells and methods according to the present invention include for example: Amyotrophic Lateral Sclerosis (ALS), Parkinson's disease, Multiple System Atrophy (MSA), Huntington's disease, Alzheimer's disease, Rett Syndrome, lysosomal storage diseases ("white matter disease" or glial/demyelination disease, as described, for example by Folkerth, J. Neuropath. Exp. Neuro., September 1999, 58:9), including Sanfilippo, Gaucher disease, Tay Sachs disease (beta hexosaminidase deficiency), other genetic diseases, multiple sclerosis (MS), brain injury or trauma caused by ischemia, accidents, environmental insult, etc., spinal cord damage, ataxia. In addition, the present invention may be used to reduce and/or eliminate the effects on the central nervous system of a stroke in a patient, which is otherwise caused by lack of blood flow or ischemia to a site in the brain of the patient or which has occurred from physical injury to the brain and/or spinal cord. Neurodegenerative diseases also include neurodevelopmental disorders including for example, autism-spectrum disorders and related neurological diseases such as schizophrenia, among numerous others.

Autoimmune diseases of the nervous system which may be treated using the cells described herein include for example, multiple sclerosis and myasthenia gravis, Guillain bar syndrome, Multiple system Atrophy (MSA; a sporadic, progressive, adult-onset neurodegenerative disorder associated with varying degrees of parkinsonism, autonomic dysfunction and cerebellar ataxia). Other autoimmune diseases are described in Kraker et al., Curr Neuropharmacol. 2011 September; 9(3): 400-408, the contents of which are incorporated herein by reference.

The cells of the present invention show enhanced immunomodulatory effect as compared to non-differentiated bone marrow derived MSCs (see Table 5 herein below). Thus, the cells of the present invention may be useful in the treatment of any immune-related or inflammatory disorder.

As used herein the phrase "inflammatory disorders" includes but is not limited to chronic inflammatory diseases and acute inflammatory diseases. Examples of such diseases and conditions are summarized infra.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12): 2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type 1 diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

According to a particular embodiment, the method described herein is for qualifying whether the cell populations are suitable for treating ALS.

The term "mesenchymal stem cell" or "MSC" is used interchangeably for adult cells which are not terminally differentiated, which can divide to yield cells that are either stem cells, or which, irreversibly differentiate to give rise to cells of a mesenchymal (chrondocyte, osteocyte and adipocyte) cell lineage. The mesenchymal stem cells of the present invention, in at least some embodiments, may be of an autologous (e.g. syngeneic) or allogeneic source.

Populations of MSCs typically express particular markers on their cell surface. According to a particular embodiment, the undifferentiated MSCs express CD105, CD73 and CD90 on the cell surface (e.g. >95% positive) and lack expression (e.g. <2% positive) of CD3, CD14, CD19, CD34, CD45, and HLA-DR as determined by flow cytometry.

Exemplary antibodies that may be used to verify the presence of mesenchymal stem cells include CD44 FITC conjugated, BD Biosciences, CD73 PE conjugated (BD Pharmingen), CD73 PE conjugated, BD Biosciences, CD90 PE-Cy5 conjugated (eBioscience) CD90 PE conjugated, BD Biosciences CD105 PE conjugated (Beckman Coulter) CD3 PerCP conjugated, BD Biosciences, CD14 FITC conjugated (eBioscience) CD14 FITC conjugated, BD Biosciences CD19 PE-Cy5 conjugated (eBioscience) CD19 FITC conjugated, BD Biosciences CD34 FITC conjugated BD Biosciences (Beckman Coulter), CD45 PE conjugated (eBioscience) CD45 PerCP conjugated, BD Biosciences and HLA-DR PE-Cy5 conjugated (BD Pharmingen). HLA-DR PerCP conjugated, BD Biosciences.

Another method for verifying the presence of mesenchymal stem cells is by showing that the cells are capable of differentiating into multi-lineages such as for example adipocytes, osteocytes and chondrocytes. This may be effected for example using Human Mesenchymal Stem Cell Functional Identification Kit (R&D Systems).

According to a preferred embodiment of this aspect of the present invention the mesenchymal stem cells are not genetically manipulated (i.e. transformed with an expression construct) to generate the cells and cell populations described herein.

It will be appreciated that the cells of the present invention, in at least some embodiments, may be derived from any stem cell, although preferably not embryonic stem (ES) cells.

Mesenchymal stem cells may be isolated from various tissues including but not limited to bone marrow, peripheral blood, blood, placenta and adipose tissue. A method of isolating mesenchymal stem cells from peripheral blood is described by Kassis et al [Bone Marrow Transplant. 2006 May; 37(10):967-76]. A method of isolating mesenchymal stem cells from placental tissue is described by Brooke G et al. [Br J Haematol. 2009 February; 144 (4):571-9].

Methods of isolating and culturing adipose tissue, placental and cord blood mesenchymal stem cells are described by Kern et al [Stem Cells, 2006; 24:1294-1301].

According to a preferred embodiment of this aspect of the present invention, the mesenchymal stem cells are human.

Bone marrow can be isolated from the iliac crest or the sternum of an individual by aspiration. Low-density BM mononuclear cells (BMMNC) may be separated by FICOLL-PAQUE density gradient centrifugation. In order to obtain mesenchymal stem cells, a cell population comprising the mesenchymal stem cells (e.g. BMMNC) may be cultured in a proliferating medium capable of maintaining and/or expanding the cells in the presence of platelet lysate. According to one embodiment the populations are plated on plastic surfaces (e.g. in a flask) and mesenchymal stem cells are isolated by removing non-adherent cells. Alternatively mesenchymal stem cell may be isolated by FACS using mesenchymal stem cell markers.

Following isolation the cells may be expanded by culturing in a proliferation medium capable of maintaining and/or expanding the isolated cells ex vivo in the presence of platelet lysate. The proliferation medium may be DMEM, alpha-MEM or DMEM/F12. Typically, the glucose concentration in the medium is about 0.5-3 grams/litre.

The culturing may be effected on any suitable surface including plastic dishes and bioreactors suitable for culturing mesenchymal stem cells.

Platelet lysate may be prepared using any method known in the art. Platelet Rich Plasma (PRP) may be derived from blood bank donations determined free of infectious agents (i.e. HIV, HTLV, HCV, HBsAg). PRP containing bags may be stored at −80° C. and thawed in a 37° C. water bath. After thawing, the Platelet Rich Plasma is typically centrifuged to remove platelet particles and membranes. The Platelet lysate supernatant may then be collected and frozen at −80° C. until use. The Platelet lysate is tested for Endotoxin, Haemoglobin, pH, Total protein, Albumin, Osmolality Sterility and Mycoplasma.

The proliferation medium may comprise additional components, including for example L-glutamine, sodium pyruvate and heparin.

It will be appreciated that preferably when the mesenchymal stem cells are human, the platelet lysate is also obtained from human cells.

According to one embodiment, the proliferation/growth medium is devoid of xeno contaminants i.e. free of animal derived components such as serum, animal derived growth factors and albumin. Thus, according to this embodiment, the culturing is performed in the absence of xeno contaminants.

An exemplary mesenchymal stem cell isolation and propagation protocol is presented in the Examples section, herein below.

As mentioned, following propagation of mesenchymal stem cells in a platelet lysate containing medium, when an adequate number of undifferentiated cells are obtained, the cells are differentiated in a differentiating medium to generating cells useful for treating diseases.

According to a particular embodiment, the cells are reseeded in a fresh proliferation/growth medium (e.g. at a density of about 6000-8000 cells per $cm^2$) for 1 day, 2 days, 3 days, 4 days or 5 days prior to addition of the differentiation medium.

The phrase "undifferentiated MSCs" refers to MSCs that have not been cultured in a medium that induces differentiation. Thus, according to at least some embodiments of the present invention, following optional proliferation, the MSCs are contacted directly with the differentiation medium without any intervening pre-differentiation steps.

For differentiation, the undifferentiated MSCs of the present invention, in at least some embodiments are incubated in a medium comprising fibroblast growth factor (FGF), platelet derived growth factor (PDGF), heregulin and c-AMP. According to this embodiment each of fibroblast growth factor (FGF), platelet derived growth factor (PDGF), heregulin and c-AMP are mixed in a single medium and the culturing is effected in a single step.

According to one embodiment, the undifferentiated MSCs of the present invention are not pre-incubated in the presence of epidermal growth factor (EGF) and/or N2 supplement prior to this step and following the expansion step.

An exemplary concentration of bFGF which is contemplated for the differentiation medium of embodiments of this invention is optionally between 5-50 ng/ml, optionally between 10-40 ng/ml, optionally between 10-25 ng/ml.

An exemplary concentration of PDGF-AA which is contemplated for the differentiation medium of embodiments of this invention is optionally between 1-30 ng/ml, optionally between 1-20 ng/ml, optionally between 1-10 ng/ml, optionally between 2.5-10 ng/ml.

An exemplary concentration of heregulin β1 which is contemplated for the differentiation medium of embodiments of this invention is optionally between 5-100 ng/ml, 10-90 ng/ml, optionally between 25-75 ng/ml and optionally between 40-60 ng/ml.

An exemplary concentration of dbc-AMP which is contemplated for the differentiation medium of embodiments of this invention is optionally between 0.5-10 mM, optionally between 0.5-5 mM and optionally between 0.5 and 2.5 mM.

According to one embodiment, the differentiating medium of this aspect of the present invention is devoid of a phosphodiesterase inhibitor (e.g. IBMX) i.e. the culturing is performed in the absence of a phosphodiesterase inhibitor.

According to another embodiment, the differentiating medium of this aspect of the present invention is devoid of triiodothyronine i.e. the culturing is performed in the absence of triiodothyronine.

Optionally, any of these embodiments and subembodiments may be combined, so that for example the differentiating medium may optionally be devoid of both a phosphodiesterase inhibitor and triiodothyronine.

Preferably, the MSCs are differentiated in the above described differentiating medium for at least one day, at least two days or at least 3 days. Preferably, the differentiating stage is not performed for more than five days.

The differentiating media used according to this aspect of the present invention are preferably xeno-free (devoid of serum) and devoid of any antibiotics i.e. the culturing is performed in the absence of xeno-contaminants.

Harvesting of the cells is typically carried out in an appropriate medium e.g. Hanks balanced salt solution (HBSS), Dulbecco Modified Eagle Medium (DMEM) RPMI, PBS etc. Hypothermic storage mediums are also contemplated (e.g. Hypothermosol).

Following the differentiation process, the cells obtained are analyzed for the expression of CD49a, wherein an amount of CD49a above a predetermined level indicative of the cell population being suitable as the therapeutic.

It will be appreciated that not all the cells obtained need to be analyzed for CD49a expression, but rather a sample thereof which provides information as to the state of the rest of the cell population.

Typically, the number of the cells in the sample is about $0.5 \times 10^6$ cells.

The number of cells obtained from a single donor is generally between $20 \times 10^6$ cells-$100 \times 10^7$ cells. Thus the number of cells may be about $20 \times 10^6$ cells, about $100 \times 10^6$ cells, about $200 \times 10^6$ cells are differentiated, about $300 \times 10^6$ cells, about $400 \times 10^6$ cells are differentiated, about $500 \times 10^6$ cells are differentiated, about $600 \times 10^6$ cells are differentiated, about $700 \times 10^6$ cells, about $800 \times 10^6$ cells, about $900 \times 10^6$ cells or about $100 \times 10^7$ cells.

As used herein, the term "CD49a" (also referred to as Integrin alpha 1) refers to the alpha 1 subunit of integrin receptor cell surface membrane protein that binds to the extracellular matrix. This protein heterodimerizes with the beta 1 subunit to form a cell-surface receptor for collagen and laminin. The heterodimeric receptor is involved in cell-cell adhesion.

The human protein sequence of CD49a is set forth in Uniprot No. P56199, NP_852478 and its mRNA sequence is set forth in NM_181501.

It will be appreciated that since CD49a forms a heterodimer on the surface of cells together with the CD49 beta1, the method of the present invention can also be effected by determining the amount of CD49beta1 on the surface of the differentiated cells.

Methods for analyzing expression of CD49a or CD49beta1 typically involve the use of antibodies which specifically recognize the antigen. Commercially available antibodies that recognize CD49a include for example those manufactured by R and D systems, Santa Cruz (Cat# SC-81733PE) or Biolegend (e.g. catalogue number 328303). The analyzing may be carried out using any method known in the art including flow cytometry, Western Blot, HPLC, in situ-PCR immunocytochemistry, mass spectrometry, radioimmunoas say, etc. According to a particular embodiment, the analyzing is effected using an antibody which specifically recognizes the protein.

For flow cytometry, the CD49a or CD49b1 antibody is attached to a fluorescent moiety and analyzed using a fluorescence-activated cell sorter (FACS).

As used herein, the term "flow cytometry" refers to an assay in which the proportion of a material (e.g. mesenchymal stem cells comprising a particular marker) in a sample is determined by labeling the material (e.g., by binding a labeled antibody to the material), causing a fluid stream containing the material to pass through a beam of light, separating the light emitted from the sample into constituent wavelengths by a series of filters and mirrors, and detecting the light.

A multitude of flow cytometers are commercially available including for e.g. Becton Dickinson FACScan and FACScalibur (BD Biosciences, Mountain View, Calif.). Antibodies that may be used for FACS analysis are taught in Schlossman S, Boumell L, et al, [Leucocyte Typing V. New York: Oxford University Press; 1995] and are widely commercially available.

For some methods, including flow cytometry, the cell populations need to be removed from the culture plate. Examples of agents that may be used to disperse the cells include, but are not limited to collagenase, dispase, accutase, trypsin (e.g. trypsin-EDTA, non-animal substitutes of trypsin such as TrypLE™), papain. Alternatively, or additionally trituration may also be performed to increase the dispersal of the cells.

An exemplary concentration of trypsin that may be used is 0.005-0.5% trypsin-EDTA. The cells may be incubated with the dispersing agent for about 5-30 minutes, at a temperature of about 37° C.

The cells are typically resuspended in a suitable medium including for example phosphate buffered saline (PBS), Hanks balanced salt solution (HBSS), Dulbecco Modified Eagle Medium (DMEM) RPMI, PBS etc.

In order to qualify that the cells are useful as a therapeutic, the amount of CD49a should be increased above a statistically significant level as compared to non-differentiated MSCs of the same donor and from the same organ.

According to a particular embodiment, in order to qualify that the cells are useful as a therapeutic, at least 80% of the cells of the population should express CD49a, more preferably at least 85% of the cells of the population should express CD49a, more preferably at least 90% of the cells of the population should express CD49a, more preferably at least 95% of the cells of the population should express CD49a.

According to another embodiment, in order to qualify that the cells are useful as a therapeutic, the level of CD49a expression (e.g. the mean fluorescent intensity) should be increased by at least two fold, more preferably at least 3 fold, more preferably at least 4 fold and even more preferably by at least 5 fold as compared to non-differentiated MSCs of the same donor and from the same organ.

It will be appreciated that using a flow cytometer, cell populations may be obtained which are more than 80% positive for CD49a. Thus, for example, cell populations may be obtained which are 85% positive for CD49a, 90% positive for CD49a, 91% positive for CD49a, 92% positive for CD49a, 93% positive for CD49a, 94% positive for CD49a, 95% positive for CD49a, 96% positive for CD49a, 97% positive for CD49a, 98% positive for CD49a, 99% positive for CD49a and even 100% positive for CD49a.

The cells may be analyzed for expression of additional cell surface markers such as CD44. Cells which have a decrease in expression by at least 1.5 or at least 2 fold or more of CD44 may be qualified as being useful as a therapeutic.

The cells may be qualified or characterized in additional ways including for example karyotype analysis, morphology, cell number and viability, gram staining and sterility.

In addition, the cells may be analyzed for their level of neurotrophic factor (NTF) secretion.

For analysis of secreted NTFs, supernatant is collected from cultures of MSCs or of NTF-secreting cells at the end of the differentiation procedure described above, and cells are harvested and counted. The amount of NTFs such as Glial Derived Neurotrophic Factor, (GDNF) or Brain Derived Neurotrophic Factor (BDNF) in the cell's culture supernatants may be quantified by using a GDNF or BDNF ELISA assay (GDNF DuoSet DY212; BDNF DuoSet DY248; R&D Systems) according to the manufacturer's protocol, for example and without limitation. The amount of IGF-1 can be quantified using an IGF ELISA assay (IGF-1 DuoSet Cat No. DY291; R&D System), for example and without limitation.

The amount of VEGF can be quantified using a VEGF ELISA assay (VEGF DuoSet R&D systems, Cat: DY293B) for example and without limitation. The amount of HGF can be quantified using an HGF ELISA assay (HGF DuoSet R&D systems, Cat: DY294) for example and without limitation.

Preferably, the amount of GDNF secreted by the cells of the present invention is increased by at least 2 fold, at least 3 fold, at least 4 fold, at least 5 fold, at least 6 fold, at least 7 fold, at least 8 fold the secretion of the same population of mesenchymal stem cells without differentiation.

The specific productivity of GDNF is from about 200-2000 pg/$10^6$ cells.

According to one embodiment, at least 50%, at least 60%, at least 70%, at least 80%, at least 90% or more of a population of the differentiated cells of the present invention secrete BDNF.

Preferably, the amount of BDNF secreted by the cells of the present invention is increased by at least 1.5 fold, at least 2 fold, at least 2.5 fold, at least 3 fold the secretion of the same population of mesenchymal stem cells without differentiation.

The specific productivity of BDNF is from about 500-8000 pg/$10^6$ cells.

The cells of the present invention differ from non-differentiated bone marrow derived mesenchymal stem cells in a variety of different ways.

Thus, for example, the cells of the present invention secrete at least 5 fold more GDF-15 than non-differentiated MSCs as measured by an ELISA assay for GDF-15 (e.g. R&D Systems, Cat # DY957 or equivalent).

Furthermore, the cells of the present invention secrete at least 10 fold, 20 fold or even 30 fold more IL-8 than non-differentiated MSCs as measured by an ELISA assay for IL-8 (e.g. R&D Systems, Cat # DY208-05 or equivalent).

In addition, the cells of the present invention comprise at least 2 fold, 4 fold, 6 fold, 8 fold or even 10 fold the amount of any one of the polypeptides 1-82, listed in Table 2. According to another embodiment, the cells of the present invention comprise at least 2 fold, 4 fold, 6 fold, 8 fold or even 10 fold the amount of each of the polypeptides 1-82, listed in Table 2. The cells of the present invention comprise at least 2 fold, 4 fold, 6 fold, 8 fold or even 10 fold less of at least one of the polypeptides 83-122, listed in Table 2. The cells of the present invention comprise at least 2 fold, 4 fold, 6 fold, 8 fold or even 10 fold less of each of the polypeptides 83-122, listed in Table 2.

The cells of the present invention may be distinguished from non-differentiated MSCs according to expression of particular genes. This may be measured by analyzing the amount of mRNA there is present in the cells encoded by the gene.

The cells of the present invention express at least 6 fold, 8 fold or even 10 fold the amount of any one of the genes 1-41, listed in Table 3. According to another embodiment, the cells of the present invention express at least 6 fold, 8 fold, 10 fold, 20 fold, or even 30 fold the amount of each of the genes 1-41, listed in Table 3. The cells of the present invention express at least 6 fold, 8 fold, 10 fold, 20 fold or even 30 fold less of at least one of the genes 42-56, listed in Table 3. The cells of the present invention express at least 6 fold, 8 fold, 10 fold or even 20 fold less of each of the genes 42-56, listed in Table 3.

The cells of the present invention differ from other bone marrow mesenchymal stem cell-derived NTF secreting cells (e.g. those disclosed in WO2009/144718—those cells are referred to herein as 2 step protocol NTFs).

Thus the cells of the present invention comprise at least 2 fold, 4 fold, 6 fold, 8 fold or even 10 fold the amount of any one of the polypeptides 1 and/or 9, listed in Table 4 as compared to 2 step protocol NTFs. The cells of the present invention comprise at least 2 fold, 4 fold, 6 fold, 8 fold or even 10 fold less of at least one of the polypeptides 2-8, listed in Table 4 as compared to 2 step protocol NTFs. The cells of the present invention comprise at least 2 fold, 4 fold, 6 fold, 8 fold or even 10 fold less of each of the polypeptides 2-8, listed in Table 4 as compared to 2 step protocol NTFs.

The cells of the present invention express at least 2 fold, 4 fold or even 6 fold the amount of any one of the genes 1-82, listed in Table 5, as compared to 2 step protocol NTFs. According to another embodiment, the cells of the present invention express at least 2 fold, 4 fold or even 6 fold the amount of each of the genes 1-82 listed in Table 5 as compared to 2 step protocol NTFs. The cells of the present invention express at least 2 fold, 4 fold or even 6 fold less of at least one of the genes 83-126, listed in Table 5 as compared to 2 step protocol NTFs. The cells of the present invention express at least 2 fold, 4 fold or even 6 fold less of each of the genes 83-126, listed in Table 5 as compared to 2 step protocol NTFs.

Other distinguishing features of the cells of the present invention are provided in WO 2014/024183, the contents of which are incorporated by reference in their entirety.

Once qualified, the cells may be labeled accordingly and preserved according to methods known in the art (e.g. frozen or cryopreserved) or may be directly administered to the subject.

As mentioned, the cells of this aspect of the present invention may be useful in treating immune or inflammatory related diseases.

Thus, according to another aspect of the present invention there is provided a method of treating an immune or inflammatory related disease in a subject in need thereof, comprising administering to the subject a therapeutically effective amount of mesenchymal stem cells which have been ex vivo differentiated to secrete neurotrophic factors, thereby treating the disease.

Examples of such diseases have been provided herein above.

According to a particular embodiment, the immune or inflammatory related disease is not a neurodegenerative disease.

According to another embodiment, the immune or inflammatory related disease is not an immune disease of the nervous system.

According to still another embodiment, the immune or inflammatory related disease is not myasthenia gravis.

Methods of obtaining mesenchymal stem cells which have been ex vivo differentiated to secrete neurotrophic factors are disclosed in WO 2014/024183, WO2006/134602 and WO2009/144718, the contents of each being incorporated herein by reference.

The cells can be administered either per se or, preferably as a part of a pharmaceutical composition that further comprises a pharmaceutically acceptable carrier.

As used herein a "pharmaceutical composition" refers to a preparation of one or more of the chemical conjugates described herein, with other chemical components such as pharmaceutically suitable carriers and excipients. The purpose of a pharmaceutical composition is to facilitate administration of a compound to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol; saline; emulsions; buffers; culture medium such as DMEM or RPMI; hypothermic storage medium containing components that scavenge free radicals, provide pH buffering, oncotic/osmotic support, energy substrates and ionic concentrations that balance the intracellular state at low temperatures; and mixtures of organic solvents with water.

Typically, the pharmaceutical carrier preserves the number of cells (e.g. is not reduced by more than 90%) in the composition for at least 24 hours, at least 48 hours or even at least 96 hours.

Herein the term "excipient" refers to an inert substance added to a pharmaceutical composition to further facilitate administration of a compound and maintain cells viability at a pre-determined temperature for a suitable period of time before transplantation/injection. Examples, without limitation, of excipients include albumin, plasma, serum and cerebrospinal fluid (CSF), antioxidants such as N-Acetylcysteine (NAC) or resveratrol.

According to a preferred embodiment of the present invention, the pharmaceutical carrier is an aqueous solution of buffer or a culture medium such as DMEM.

Techniques for formulation and administration of drugs may be found in "Remington's Pharmaceutical Sciences," Mack Publishing Co., Easton, Pa., latest edition, which is incorporated herein by reference.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals.

The data obtained from these in vitro and cell culture assays and animal studies can be used in formulating a range of dosage for use in human. Further information may be obtained from clinical studies—see for example Salem H K et al., Stem Cells 2010; 28:585-96; and Uccelli et al. Lancet Neurol. 2011; 10:649-56).

The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p. 1.

For injection, the active ingredients of the pharmaceutical composition may be formulated in aqueous solutions, preferably in physiologically compatible buffers such as Hank's solution, Ringer's solution, or physiological salt buffer and additional agents as described herein above.

Dosage amount and interval may be adjusted individually to levels of the active ingredient which are sufficient to effectively cause an immunomodulatory effect. Dosages necessary to achieve the desired effect will depend on individual characteristics and route of administration.

Depending on the severity and responsiveness of the condition to be treated, dosing of cells can be of a single or a plurality of administrations, with course of treatment lasting from several days to several weeks or months depending when diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition.

The cells of the present invention, in at least some embodiments, may be prepackaged in unit dosage forms in a syringe ready for use. The syringe may be labeled with the name of the cells and their source. The labeling may also comprise information related to the function of the cells (e.g. the amount of neurotrophic factor secreted therefrom). The syringe may be packaged in a packaging which is also labeled with information regarding the cells.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Analysis of Surface Markers in Differentiated Cells

Materials and Methods

Bone Marrow Aspiration (BMA): Fresh bone marrow was aspirated according to the routine Medical Center procedure from the patient's iliac-crest under local anesthesia and sedation by an anesthetist. Bone marrow (30-60 ml) was aspirated using aspiration needles into heparin containing tubes.

Separation of MNC and Enrichment of MSC: This step involves separation of mononuclear cells (MNC) from total bone marrow.

The Human Multipotent Mesenchymal stromal cells (MSC), estimated to comprise 0.01% of total bone marrow MNC, are enriched in-vitro from MNC, by virtue of their ability to adhere to plastic.

Bone marrow aspirate was diluted 1:1 (v:v) in Hank's Balanced Salt Solution (HBSS), and MNC were separated from total bone marrow cells by Ficoll density gradient centrifugation.

MNC were counted and cell number and viability were determined by the Trypan Blue dye exclusion test. The yield of MNC recovered after density gradient centrifugation varied between donors and depends on the volume of bone marrow collected. The yield of MNC recovered from 30-50 ml of bone marrow aspirate of ALS patients ranged between 70-400×10$^6$ MNC and was sufficient for isolating the number of MSC necessary for the entire production process.

The medium used for seeding the primary bone marrow mononuclear cells and propagating the MSCs throughout the production process was designated Platelets Growth medium (PM). The PM medium was used throughout the MSC production process (Passage 0-Passage 4) [P0-P4] and contained low glucose DMEM, L-Glutamine sodium pyruvate, heparin and platelet lysate.

MNCs were seeded at a density of 100,000-400,000 cells/cm$^2$ in flasks in PM/flask and incubated overnight in a 37° C./5% CO$_2$ humidified incubator. The next day, the cell culture was examined under the microscope. At this stage, non-adherent, mononuclear cell were floating in the culture supernatant and plastic-adherent MSC were attached to the flask surface. The culture supernatant containing the non-adherent mononuclear cells was removed, and the adherent cells were gently washed with DMEM. The DMEM was discarded and fresh PM was added to each flask containing the plastic adherent MSC cells. The process phase from MNC seeding to MSC harvesting was designated Passage 0 (P0).

The P0 cells were incubated in a 37° C./5% CO$_2$ humidified incubator and PM was replaced twice a week, with fresh PM, until the culture was sub-confluent.

Propagation of MSC: Primary cultures of MSC were grown in-vitro as a single cell layer attached to a plastic substrate. Once the available substrate surface was covered by cells (a confluent culture), growth slowed and then ceased. Thus, in order to keep the cells healthy and actively growing, it was necessary to subculture them at regular intervals, when the culture was sub-confluent. Each subculture cycle is designated Passage. The MSC culture was passaged at a density of 500-2,000 cells/cm$^2$.

For passaging MSC, the culture supernatant was removed from the flask and Trypsin (TrypLE™ Select, Invitrogen) was added to each flask. The flask was incubated for several minutes at 37° C. and the resulting cell suspension was collected from the flask into centrifuge tubes and DMEM was added to each flask for diluting the Trypsin and collecting the remaining cells.

The cell suspension was centrifuged re-suspended in PM, counted and reseeded at a density of 500-2,000 cells/cm$^2$ in new culture vessels. The cultures were then incubated in a 37° C./5% CO$_2$ humidified incubator.

In the course of each passage the PM was replaced every 3-4 days, by removing all the culture supernatant and replacing it with the same volume of fresh PM.

Induction of Differentiation: MSC were seeded for induction of differentiation in PM at a concentration of about 6,000-8,000 cells/cm$^2$. Three days later, differentiation was induced by replacing the PM with differentiation medium (S2M) containing low glucose DMEM supplemented with 1 mM dibutyryl cyclic AMP (cAMP), 20 ng/ml human Basic Fibroblast Growth Factor (hbFGF), 5 ng/ml human platelet derived growth factor (PDGF-AA), and 50 ng/ml human Heregulin β1. The culture was maintained in differentiation medium for 3 days until harvesting.

MSC-NTF cells were harvested 24 hours before the end of differentiation (Day 2) and/or at the end of differentiation (Day 3). MSC cell were harvested from the same donor or patient at the same passage at the same time.

Sample Preparation, Acquisition and Analysis: Cells were suspended in PBS at a concentration of 0.5-1×10$^6$ cells/tube and stained for 30 minutes on ice with a mouse monoclonal Antibody to Integrin α1 (IgG1, clone TS2/7.1.1, Santa Cruz Cat# SC-81733PE). The isotype control was a Mouse IgG1 k-PE conjugated, isotype control (clone MOPC-21, Cat#555749 BD Biosciences). Cells were analyzed by Flow Cytometry (Cytomics FC 500, Beckman Coulter, Inc.) and the data analyzed using the CXP software (Beckman Coulter, Inc.).

Results

The expression of Integrin alpha 1 (CD49a) was studied on the surface of MSC and MSC cells induced to secrete neurotropic factors (MSC-NTF cells).

At the end of the differentiation process (Day 3) about 90±4.43% (mean±standard deviation) of the MSC-NTF cell population expressed CD49a as compared to 68.75±4.29% (mean±standard deviation) of the non-differentiated MSC cell population of the same donor (n=8). The difference between the two populations is highly significant (p<0.0001, Day 3, Table 1A).

On Day 3, Mean Fluorescence Intensity (MFI) was also found to significantly increase in MSC-NTF cells populations from 2.75±0.48% (mean±standard deviation) of MSC to 13.2±4.77% (mean±standard deviation) for MSC-NTF cells, an average 4.87±1.56 fold induction (n=8, Table 1A).

One day prior to the end of differentiation (Day 2) 90.55±6.62% (mean±standard deviation) of the MSC-NTF cell populations expressed CD49a as compared to 73±6% (mean±standard deviation) of the non-differentiated MSC cell population of the same donor. The difference between the two populations is highly significant (p<0.005, Day 2, Table 1A).

On Day 2, Mean Fluorescence Intensity (MFI) was also found to significantly increase in MSC-NTF cells populations from 2.84±0.98% (mean±standard deviation) of MSC to 11.58±7.18% (mean±standard deviation) for MSC-NTF cells an average 3.77±1.43 fold induction (n=4, Table 1A).

TABLE 1A

|  | MSC | | MSC-NTF | | p value for difference in | MFI Fold | |
| --- | --- | --- | --- | --- | --- | --- | --- |
|  | % Positives | MFI | % Positives | MFI | % positives | induction | n |
| Day 2 | 73 ± 6 | 2.84 ± 0.98 | 90.55 ± 6.62 | 11.58 ± 7.18 | p < 0.005 | 3.77 ± 1.43 | 4 |
| Day 3 | 68.75 ± 4.29 | 2.75 ± 0.48 | 90 ± 4.43 | 13.2 ± 4.77 | p < 0.0001 | 4.87 ± 1.56 | 8 |

Two additional experiments were performed to corroborate these results. For the first experiment, at the end of the differentiation process (Day 3), about 80.9% of the MSC-NTF cell population expressed CD49a as compared 56.05% of the non-differentiated MSC cell population of the same donor (Table 1B). For the second experiment, at the end of the differentiation process (Day 3) about 89% of the MSC-NTF cell population expressed CD49a as compared 60% of the non-differentiated MSC cell population of the same donor (Table 1B).

TABLE 1B

| | CD49a % positives | |
| --- | --- | --- |
| Exp# | MSC | MSC-NTF |
| 1 | 56.05 | 80.9 |
| 2 | 60 | 89 |

Example 2

Comparison of MSC-NTFs with Non-differentiated MSCs

Materials and Methods

Induction of Differentiation: as detailed in Example 1.

Measurement of Growth/Differentiation Factor-15 (GDF-15) and Interleukin 8 (IL-8) The amount of GDF-15 and IL-8 in the cell's culture supernatants at the end of differentiation were quantified by using the GDF-15 ELISA assay (GDF-15 DuoSet DY957; R&D Systems) the IL-8 ELISA assay (IL-8 DuoSet DY208; R&D Systems) according to the manufacturer's protocol, for example and without limitation.

Proteomics

Proteolysis: The protein were extracted from the cell pellets in 9M Urea, 400 mM Ammonium bicarbonate and 10 mM DTT and two cycles of sonication. 20 µg protein from each sample were reduced with 2.8 mM DTT (60° C. for 30 min), modified with 8.8 mM iodoacetamide in 400 mM ammonium bicarbonate (in the dark, room temperature for 30 min) and digested in 2 M Urea, 25 mM ammonium bicarbonate with modified trypsin (Promega) at a 1:50 enzyme-to-substrate ratio, overnight at 37° C. An additional second trypsinization was done for 4 hours.

Mass Spectrometry Analysis: The tryptic peptides were desalted using C18 tips (Harvard) dried and re-suspended in 0.1% Formic acid.

The peptides were resolved by reverse-phase chromatography on 0.075×180-mm fused silica capillaries (J&W) packed with Reprosil reversed phase material (Dr Maisch GmbH, Germany). The peptides were eluted with linear 180 minutes gradient of 5 to 28% 5 minutes gradient of 28 to 95% and 25 minutes at 95% acetonitrile with 0.1% formic acid in water at flow rates of 0.15 µl/min. Mass spectrometry was performed by Q Exactive plus mass spectrometer (Thermo) in a positive mode using repetitively full MS scan followed by collision induces dissociation (CID) of the 10 most dominant ions selected from the first MS scan.

The mass spectrometry data from three biological repeats was analyzed using the MaxQuant software 1.4.1.2 (Mathias Mann's group) vs. the human section of the Uniprot database with 1% FDR. The data was quantified by label free analysis using the same software.

The intensity data was transformed to log 2 in order to get a normal distribution.

Welch T-Test with Permutation-based FDR, (with 250 randomization, Threshold value=0.05) between the A and the B groups was done using the Preseuse 1.4. Same software was used for additional annotations and data correlation.

Genearray: Genearray analyses were run using the Expression Array Gene ST 2.0 GeneChip® Human Gene 2.0 ST Array (Affymetrix).

Cell pellets were resuspended in RNA Protect (Qiagen). Total RNA was extracted using the RNeasy Plus Mini kit (Qiagen, cat#74134). RNA Quality was measured using TapeStation (Agilent). 250 ng of RNA were labeled using GeneChip® WT PLUS Reagent Kit (Affymetrix, cat#902280), following manufacturer manual (Affymetrix cat#703174 Rev. 2). Briefly, cDNA was synthesized from the RNA using random primers, while adding a T7 promoter tail. cRNA was then generated by in vitro transcription using T7-RNA-Polymerase. Single-stranded cDNA was synthesized, then fragmented and end-labeled. 3.5 ug were hybridized to a GeneChip® Human Gene 2.0 ST Arrays (Affymetrix, cat#902499). Arrays were washed and stained using the GeneChip Hybridization Wash and Stain kit (Affymetrix cat#900720) and scanned. Images were subjected to visual inspection, followed by quantitation (RMA-gene), normalization (Sketch-Quantile) and QC using Expression Console build 1.3.1.187 (Affymetrix). All parameters passed QC metrics and no outliers were observed. A list of deferentially expressed genes was generated using One-Way Between-Subject ANOVA (Unpaired) with the Transcriptome Analysis Console 2.0 (Affymetrix).

The experiment compared the untreated MSC control and MSC-NTF cells induced to differentiate by the one step protocol described for Example 1. Samples from three unrelated subjects were analyzed for each condition. The overall difference between individuals was found to be smaller than between conditions.

Results

It was found that in 23 ALS patients, specific productivity of GDF-15 was in the range of 225.79±99.72 pg/ml/$\times 10^6$ cells in MSC and was found to increase to 1257.20±890.60 pg/ml/$\times 10^6$ in MSC-NTF cells of the same patient prior to differentiation, a 9.4 fold average increase (FIG. 2A).

Further, it was found that MSC-NTF cells of ALS patients secreted significant amounts of IL-8 (an average of 81±43 ng/ml/×10⁶ cells) as compared to MSC of the same patient prior to differentiation, a 170 fold average increase (FIG. 2B).

Bone marrow derived MSCs from ALS patients were analyzed via proteomics both prior to and following differentiation using the protocol described in the materials and methods.

The most significantly up- or down-regulated proteins, based on identification by at least two peptides in three repeats using Mass spec, normalized for the intensity of the detection of the protein are presented in Table 2, herein below.

TABLE 2

| | Protein IDs | Protein names | Gene names | welch p value_PA1 vs PB1 | welch Difference_PA1 vs PB1 |
|---|---|---|---|---|---|
| 1 | Q04828; H0Y804; A6NHU4; P17516 | Aldo-keto reductase family 1 member C1 | AKR1C1 | 0.025239 | −4.27165 |
| 2 | P36222; H0Y3U8 | Chitinase-3-like protein 1 | CHI3L1 | 0.00333 | −8.03492 |
| 3 | O14684 | Prostaglandin E synthase | PTGES | 0.03174 | −6.82836 |
| 4 | P09601; B1AHA8 | Heme oxygenase 1 | HMOX1 | 0.004332 | −3.58814 |
| 5 | Q16678 | Cytochrome P450 1B1 | CYP1B1 | 0.003662 | −7.19957 |
| 6 | Q7LBR1 | Charged multivesicular body protein 1b | CHMP1B | 0.003375 | −4.41248 |
| 7 | Q9BS40 | Latexin | LXN | 0.01834 | −3.01403 |
| 8 | P01033; Q5H9A7; H0Y789; Q5H9B5; Q5H9B4 | Metalloproteinase inhibitor 1 | TIMP1 | 0.007288 | −3.62584 |
| 9 | P48307; H7C4A3 | Tissue factor pathway inhibitor 2 | TFPI2 | 1 | ND |
| 10 | Q8WUJ3; H0YL56; H0YCE1 | Protein KIAA1199 | KIAA1199 | 0.014234 | −3.67028 |
| 11 | P42330; S4R3Z2; S4R3D5 | Aldo-keto reductase family 1 member C3 | AKR1C3 | 0.02981 | −3.86375 |
| 12 | P17301 | Integrin alpha-2 | ITGA2 | 0.001484 | −5.15083 |
| 13 | O94875; H7BZK1; Q9BX66 | Sorbin and SH3 domain-containing protein 2 | SORBS2 | 0.013196 | −4.11166 |
| 14 | P52895; B4DK69; S4R3P0 | Aldo-keto reductase family 1 member C2 | AKR1C2 | 0.026833 | −4.96764 |
| 15 | P41221; C9J8I8; Q9H1J7; F5H7Q6; F5H364; F5H034; O00755 | Protein Wnt-5a | WNT5A | 0.010376 | −3.1782 |
| 16 | Q9HCJ1; D6RGI5 | Progressive ankylosis protein homolog | ANKH | 0.018078 | −3.77482 |
| 17 | P07093; C9JN98; C9K031 | Glia-derived nexin | SERPINE2 | 0.005989 | −3.61762 |
| 18 | Q5VYS4; H0Y831 | Mesenteric estrogen-dependent adipogenesis protein | MEDAG | 0.003767 | −4.08412 |
| 19 | Q13228; H0Y532; A6PVX1; F2Z2W8; F8WCR4; C9JVL0; F8WBA9 | Selenium-binding protein 1 | SELENBP1 | 0.024781 | −3.34893 |
| 20 | O00194; K7ES41; K7EJ38 | Ras-related protein Rab-27B | RAB27B | 0.023078 | −3.70819 |
| 21 | P17676 | CCAAT/enhancer-binding protein beta | CEBPB | 0.008846 | −3.43367 |
| 22 | Q99988 | Growth/differentiation factor 15 | GDF15 | 1 | ND |
| 23 | Q8IWB1; X6RK76 | Inositol 1,4,5-trisphosphate receptor-interacting protein | ITPRIP | 0.003773 | −5.21981 |
| 24 | P02675; D6REL8; CON_P02676 | Fibrinogen beta chain; Fibrinopeptide B; Fibrinogen beta chain | FGB | 1 | −6.5007 |
| 25 | P10253; I3L0S5; I3L3L3 | Lysosomal alpha-glucosidase; 76 kDa lysosomal alpha-glucosidase; 70 kDa lysosomal alpha-glucosidase | GAA | 0.011612 | −3.59936 |
| 26 | C9JEU5; P02679; C9JC84; C9JPQ9; C9JU00 | Fibrinogen gamma chain | FGG | 0.012628 | −6.08619 |

TABLE 2-continued

| | Protein IDs | Protein names | Gene names | welch p value_PA1 vs PB1 | welch Difference_PA1 vs PB1 |
|---|---|---|---|---|---|
| 27 | Q8IV20; A2A3Z5 | Laccase domain-containing protein 1 | LACC1 | 0.044734 | −4.52527 |
| 28 | Q96AQ6; Q5T173 | Pre-B-cell leukemia transcription factor-interacting protein 1 | PBXIP1 | 0.004564 | −3.39635 |
| 29 | O15118; K7EQ23 | Niemann-Pick C1 protein | NPC1 | 0.010158 | −4.33114 |
| 30 | Q7Z2X4 | PTB-containing, cubilin and LRP1-interacting protein | PID1 | 0.026791 | −4.2971 |
| 31 | P61587; E9PFH1; Q53RZ3 | Rho-related GTP-binding protein RhoE | RND3 | 0.029183 | −3.05365 |
| 32 | P32189; Q14409; F8WC39; A6NP46; C9JLT1; F8WDA9; F8WBI8; F8WF44; H7BYD2; H7C2A0 | Glycerol kinase; Putative glycerol kinase 3 | GK; GK3P | 0.018576 | −4.98535 |
| 33 | P04003; A6PVY5; F2Z2V7 | C4b-binding protein alpha chain | C4BPA | 1 | −5.46453 |
| 34 | Q8N726 | Cyclin-dependent kinase inhibitor 2A, isoform 4 | CDKN2A | 1 | ND |
| 35 | A0JP02; B4DJX4; Q9HAU0; E7EME8; H0YG48; H0YGJ6 | Pleckstrin homology domain-containing family A member 5 | PLEKHA5 | 0.022674 | −3.89935 |
| 36 | P43003; M0R063; P48664; E7EUS7; E7EUV6; M0QY32; M0R106; E7EV13 | Excitatory amino acid transporter 1 | SLC1A3 | 0.036812 | −3.63458 |
| 37 | F5GYK4; O00142; E5KNQ5; H3BP77; J3KS73; J3QL12; J3QRP0; J3KRW8 | Thymidine kinase 2, mitochondrial | TK2 | 0.00388 | −4.92515 |
| 38 | P98066 | Tumor necrosis factor-inducible gene 6 protein | TNFAIP6 | 1 | ND |
| 39 | P06280; V9GYN5 | Alpha-galactosidase A | GLA | 0.047612 | −4.14468 |
| 40 | P38936; J3KQV0 | Cyclin-dependent kinase inhibitor 1 | CDKN1 | 1 | ND |
| 41 | P08476 | Inhibin beta A chain | INHBA | 1 | ND |
| 42 | Q9UHE8 | Metalloreductase STEAP1 | STEAP1 | 1 | ND |
| 43 | Q8WWI5 | Choline transporter-like protein 1 | SLC44A1 | 0.009593 | −3.14327 |
| 44 | P01024; CON_Q2UVX4; M0R0Q9; M0QYC8; M0QXZ3 | Complement C3; Complement C3 beta chain; Complement C3 alpha chain; C3a anaphylatoxin; Acylation stimulating protein; Complement C3b alpha chain; Complement C3c alpha chain fragment 1; Complement C3dg fragment; Complement C3g fragment; Complement C3d fragment; Complement C3f fragment; Complement C3c alpha chain fragment 2 | C3 | 0.01925 | −4.77651 |
| 45 | Q9ULG6; H3BN32 | Cell cycle progression protein 1 | CCPG1 | 0.028133 | −3.63365 |
| 46 | P05165; H0Y5U0; Q5JTW6 | Propionyl-CoA carboxylase alpha chain, mitochondrial | PCCA | 0.023694 | −3.97258 |
| 47 | P14923 | Junction plakoglobin | JUP | 0.001268 | −4.30589 |

TABLE 2-continued

| | Protein IDs | Protein names | Gene names | welch p value_PA1 vs PB1 | welch Difference_PA1 vs PB1 |
|---|---|---|---|---|---|
| 48 | Q9Y4F1; C9JME2; M0QXT1; M0QYB0; H0Y783; M0R262 | FERM, RhoGEF and pleckstrin domain-containing protein 1 | FARP1 | 0.014285 | −3.70348 |
| 49 | Q9NRZ5; Q6AI25; G3XAF1; Q5TEE8 | 1-acyl-sn-glycerol-3-phosphate acyltransferase delta | AGPAT4 | 0.00875 | −3.07989 |
| 50 | Q9H098; C9J6N5; C9JQ40; C9JW51; C9J3Q3; X6RET8; C9JP05; F8WCJ2; C9JYP1; C9J6Y8 | Protein FAM107B | FAM107B | 1 | ND |
| 51 | P18428 | Lipopolysaccharide-binding protein | LBP | 0.021616 | −3.41834 |
| 52 | H0Y4R5; Q5SNT2 | Transmembrane protein 201 | TMEM201 | 1 | ND |
| 53 | Q8N6G5 | Chondroitin sulfate N-acetylgalactosaminyl transferase 2 | CSGALNACT2 | 1 | ND |
| 54 | Q8NFT2; B5MC02; C9JLP2 | Metalloreductase STEAP2 | STEAP2 | 0.033114 | −3.16521 |
| 55 | P35475; D6REB5; H0Y9B3; D6R9D5; D6RBD5; H0Y9R9 | Alpha-L-iduronidase | IDUA | 1 | ND |
| 56 | P05546 | Heparin cofactor 2 | SERPIND1 | 1 | −3.13676 |
| 57 | H7BXR3; H7C1R7; H7BZX1; C9J3W4; C9JL62; C9IZ89 | | SORBS2 | 1 | ND |
| 58 | Q5QJ74; E9PP54; E9PNS0; E9PJJ0; B3KNB6; G3V147 | Tubulin-specific chaperone cofactor E-like protein | TBCEL | 1 | ND |
| 59 | P36269; H7C1X2 | Gamma-glutamyltransferase 5; Gamma-glutamyltransferase 5 heavy chain; Gamma-glutamyltransferase 5 light chain | GGT5 | 1 | ND |
| 60 | Q13219 | Pappalysin-1 | PAPPA | 1 | ND |
| 61 | Q9P2B2 | Prostaglandin F2 receptor negative regulator | PTGFRN | 1 | ND |
| 62 | E7EW77; E7EP65; Q9NYB9; J3KNB2; E9PEZ7; H7C3Q7; H0Y6B5; F8WBL5; F8WAQ3; F8WEB9; E7EUA1; F8WAU3; F8WCD7; F8WAZ8 | Abl interactor 2 | ABI2 | 1 | ND |
| 63 | P58335 | Anthrax toxin receptor 2 | ANTXR2 | 0.017357 | −3.75924 |
| 64 | P51884; CON_Q05443 | Lumican | LUM | 1 | ND |
| 65 | Q86UX7; F5H1C6; F5H3I6 | Fermitin family homolog 3 | FERMT3 | 1 | ND |
| 66 | P35869; E5RGQ2; G3V143; E5RFG4; A9YTQ3 | Aryl hydrocarbon receptor | AHR | 0.029594 | −3.42358 |
| 67 | P56199 | Integrin alpha-1 | ITGA1 | 1 | ND |
| 68 | P35354; Q6ZYK7 | Prostaglandin G/H synthase 2 | PTGS2 | 1 | ND |
| 69 | Q96MK3 | Protein FAM20A | FAM20A | 1 | ND |
| 70 | Q96CC6; F8WCF7; B8ZZ07; F6XBT0; F8WBS4 | Inactive rhomboid protein 1 | RHBDF1 | 1 | ND |
| 71 | P33897; H0Y7L9 | ATP-binding cassette sub-family D member 1 | ABCD1 | 1 | −3.15122 |
| 72 | Q05707; J3QT83; Q4G0W3 | Collagen alpha-1(XIV) chain | COL14A1 | 0.047499 | −3.24857 |
| 73 | P43490; Q5SYT8; F5H246; C9JG65; C9JF35 | Nicotinamide phosphoribosyltransferase | NAMPT; NAMPTL | 0.010112 | −2.84468 |

TABLE 2-continued

| | Protein IDs | Protein names | Gene names | welch p value_PA1 vs PB1 | welch Difference_PA1 vs PB1 |
|---|---|---|---|---|---|
| 74 | P17302 | Gap junction alpha-1 protein | GJA1 | 0.005458 | −2.72582 |
| 75 | P07711; Q5T8F0; Q5NE16; O60911 | Cathepsin L1; Cathepsin L1 heavy chain; Cathepsin L1 light chain | CTSL1 | 0.023268 | −2.64752 |
| 76 | P11498; E9PRE7; E9PS68 | Pyruvate carboxylase, mitochondrial | PC | 0.002932 | −2.77116 |
| 77 | P17677 | Neuromodulin | GAP43 | 0.041471 | −2.55059 |
| 78 | Q7LG56; H0YAV1 | Ribonucleoside-diphosphate reductase subunit M2 B | RRM2B | 0.015477 | −2.57625 |
| 79 | Q02252; G3V4Z4 | Methylmalonate-semialdehyde dehydrogenase [acylating], mitochondrial | ALDH6A1 | 0.00472 | −2.98955 |
| 80 | E9PF16; Q96CM8; D6RF87 | Acyl-CoA synthetase family member 2, mitochondrial | ACSF2 | 0.036886 | −2.88375 |
| 81 | P23786 | Carnitine O-palmitoyltransferase 2, mitochondrial | CPT2 | 0.040208 | −2.55565 |
| 82 | C9JGI3; P19971 | Thymidine phosphorylase | TYMP | 0.032844 | −2.93769 |
| 83 | F5H6B2; Q9UHN6 | Transmembrane protein 2 | TMEM2 | 1 | ND |
| 84 | P10915; D6RBS1 | Hyaluronan and proteoglycan link protein 1 | HAPLN1 | 1 | ND |
| 85 | Q6UVK1 | Chondroitin sulfate proteoglycan 4 | CSPG4 | 1 | ND |
| 86 | P01130; J3KMZ9; H0YMD1; H0YMQ3; H0YM92 | Low-density lipoprotein receptor | LDLR | 1 | ND |
| 87 | G3V511; G3V3X5; Q14767 | Latent-transforming growth factor beta-binding protein 2 | LTBP2 | 1 | 4.404051 |
| 88 | F5H855; P56945; Q14511 | Breast cancer anti-estrogen resistance protein 1 | BCAR1 | 1 | 4.176916 |
| 89 | O95801; Q5TA95 | Tetratricopeptide repeat protein 4 | TTC4 | 1 | ND |
| 90 | O95347; Q5T821 | Structural maintenance of chromosomes protein 2 | SMC2 | 1 | ND |
| 91 | P43007 | Neutral amino acid transporter A | SLC1A4 | 1 | ND |
| 92 | P26022 | Pentraxin-related protein PTX3 | PTX3 | 1 | 3.989578 |
| 93 | Q8TB03 | Uncharacterized protein CXorf38 | CXorf38 | 1 | ND |
| 94 | Q8IZ07; S4R3D2; H0YIN8; F8W150; S4R3U2; Q6ZTN6 | Ankyrin repeat domain-containing protein 13A | ANKRD13A | 1 | 5.833572 |
| 95 | Q9NX58 | Cell growth-regulating nucleolar protein | LYAR | 1 | ND |
| 96 | P02790 | Hemopexin | HPX | 1 | ND |
| 97 | Q6ZN40; H0YL80; H0YLS7 | | TPM1 | 0.004913 | 3.131315 |
| 98 | P08123 | Collagen alpha-2(I) chain | COL1A2 | 0.008003 | 3.385308 |
| 99 | K7ENT6; K7ERG3 | | TPM4 | 0.034608 | 3.634858 |
| 100 | P02452; CON_Q862S4; I3L3H7; P02458 | Collagen alpha-1(I) chain | COL1A1 | 0.008651 | 5.24923 |
| 101 | P20337 | Ras-related protein Rab-3B | RAB3B | 0.00338 | 3.365877 |
| 102 | P0C0L5; F5GXS0 | Complement C4-B; Complement C4 beta chain; Complement C4-B alpha chain; C4a anaphylatoxin; C4b-B; C4d-B; Complement C4 gamma chain | C4B | 0.035673 | 4.70512 |
| 103 | Q14566 | DNA replication licensing factor MCM6 | MCM6 | 0.015309 | 3.802778 |

TABLE 2-continued

| | Protein IDs | Protein names | Gene names | welch p value_PA1 vs PB1 | welch Difference_PA1 vs PB1 |
|---|---|---|---|---|---|
| 104 | Q9H7C4; C9JTN4; C9JSS1 | Syncoilin | SYNC | 0.04319 | 3.910519 |
| 105 | P02787; C9JVG0; H7C5E8; F8WEK9; F8WCI6; C9JB55; F8WC57; CON_Q29443; CON_Q0IIK2 | Serotransferrin | TF | 0.013404 | 6.25542 |
| 106 | P49736; H7C4N9; C9J013; C9JZ21; F8WDM3 | DNA replication licensing factor MCM2 | MCM2 | 0.040152 | 4.184367 |
| 107 | P33993; C9J8M6 | DNA replication licensing factor MCM7 | MCM7 | 0.035577 | 3.315128 |
| 108 | P33991; E5RG31; E5RFJ8; E5RFR3 | DNA replication licensing factor MCM4 | MCM4 | 0.033108 | 3.523307 |
| 109 | P25205; B4DWW4; J3KQ69; Q7Z6P5 | DNA replication licensing factor MCM3 | MCM3 | 0.040364 | 3.55418 |
| 110 | E9PD53; Q9NTJ3; C9JR83; C9JVD8; C9J578; C9J9E4 | Structural maintenance of chromosomes protein; Structural maintenance of chromosomes protein 4 | SMC4 | 0.011999 | 3.016034 |
| 111 | P26006; H0YA49; H0YA32; K7EMU3; D6R9X8 | Integrin alpha-3; Integrin alpha-3 heavy chain; Integrin alpha-3 light chain | ITGA3 | 0.030181 | 3.334243 |
| 112 | P01023; CON_ENSEMBL:ENSBTAP00000024146; P20742; H0YFH1; F8W7L3; F5H1E8 | Alpha-2-macroglobulin | A2M | 0.000365 | 8.539567 |
| 113 | O95361; B3KP96; H0Y626; K7ENN8; Q309B1; K7EL43; I3L3K9; I3L2F3; J3QL38; J3QKY5 | Tripartite motif-containing protein 16 | TRIM16 | 1 | 3.605912 |
| 114 | P05121 | Plasminogen activator inhibitor 1 | SERPINE1 | 1 | 5.247232 |
| 115 | Q15021; E7EN77 | Condensin complex subunit 1 | NCAPD2 | 0.041189 | 4.251724 |
| 116 | H7BYY1; F5H7S3; B7Z596; H0YL42; H0YK20 | | TPM1 | 0.008933 | 2.809683 |
| 117 | P08243; F8WEJ5; C9J057; C9JT45; C9JM09; C9JLN6 | Asparagine synthetase [glutamine-hydrolyzing] | ASNS | 0.011498 | 2.974403 |
| 118 | O43294; H3BQC4; H3BSN4; I3L209; H3BS04; H3BN49 | Transforming growth factor beta-1-induced transcript 1 protein | TGFB1I1 | 0.014001 | 2.818781 |
| 119 | P20908; H7BY82; P12107; C9JMN2; H0YIS1; Q4VXY6; P13942; P25940 | Collagen alpha-1(V) chain | COL5A1 | 0.019362 | 2.800896 |
| 120 | Q5H909; Q9UNF1; Q5H907 | Melanoma-associated antigen D2 | MAGED2 | 0.011154 | 2.607765 |
| 121 | P35520; C9JMA6; H7C2H4 | Cystathionine beta-synthase; Cysteine synthase | CBS | 0.029219 | 2.717574 |
| 122 | P23921; E9PL69 | Ribonucleoside-diphosphate reductase large subunit | RRM1 | 0.033696 | 2.537958 |

Bone marrow derived MSCs from ALS patients were analyzed via Genearray both prior to and following differentiation using the protocol described in the materials and methods.

Out of a total of 48,226 genes that were analyzed, 1623 genes were found to be differentially expressed—518 genes were found to be up-regulated and 567 genes were found to be down-regulated.

Table 3, herein below provides a list of exemplary genes that were significantly up or down regulated following differentiation.

TABLE 3

| | Fold Change (linear) | ANOVA p-value | Gene Symbol | Description |
|---|---|---|---|---|
| 1 | 87.97 | 0.000045 | SLC16A6 | solute carrier family 16, member 6 (monocarboxylic acid transporter 7); NULL |
| 2 | 66.16 | 0.000142 | IL8 | interleukin 8 |
| 3 | 48.62 | 0.000019 | MMP13 | matrix metallopeptidase 13 (collagenase 3) |
| 4 | 47.05 | 0.000048 | BMP2 | bone morphogenetic protein 2 |
| 5 | 37.07 | 0.002339 | CXCL6 | chemokine (C—X—C motif) ligand 6 |
| 6 | 30.74 | 0.000005 | RASD1 | RAS, dexamethasone-induced 1 |
| 7 | 29.67 | 0.000006 | IL11 | interleukin 11 |
| 8 | 28.33 | 4.29E−07 | PCSK1 | proprotein convertase subtilisin/kexin type 1 |
| 9 | 27.52 | 0.001772 | TFPI2 | tissue factor pathway inhibitor 2 |
| 10 | 27.43 | 0.001103 | AREG | amphiregulin; amphiregulin B |
| 11 | 26.99 | 0.000544 | PTGES | prostaglandin E synthase |
| 12 | 26.35 | 0.004312 | CHI3L1 | chitinase 3-like 1 (cartilage glycoprotein-39) |
| 13 | 25.85 | 0.009822 | CXCL5 | chemokine (C—X—C motif) ligand 5 |
| 14 | 22.3 | 0.000954 | AREGB | amphiregulin B; amphiregulin |
| 15 | 22.18 | 0.000314 | | |
| 16 | 21.76 | 0.000641 | COL10A1 | collagen, type X, alpha 1 |
| 17 | 20.32 | 0.007707 | | |
| 18 | 16.09 | 0.000037 | PTHLH | parathyroid hormone-like hormone |
| 19 | 15.1 | 0.000566 | TNFAIP6 | tumor necrosis factor, alpha-induced protein 6 |
| 20 | 14.88 | 0.00001 | SMOC1 | SPARC related modular calcium binding 1 |
| 21 | 13.65 | 0.000138 | ABCA1 | ATP-binding cassette, sub-family A (ABC1), member 1 |
| 22 | 13.59 | 0.000006 | MEDAG | mesenteric estrogen-dependent adipogenesis |
| 23 | 12.67 | 0.000898 | OTTHUMG00000037425 | NULL |
| 24 | 12.49 | 0.000627 | ABCA6 | ATP-binding cassette, sub-family A (ABC1), member 6; NULL |
| 25 | 12.25 | 0.000573 | IL1B | interleukin 1, beta; NULL |
| 26 | 11.53 | 0.007657 | MMP3 | matrix metallopeptidase 3 (stromelysin 1, progelatinase); NULL |
| 27 | 11.52 | 0.000001 | SMOX | spermine oxidase; NULL |
| 28 | 11.46 | 0.000021 | GAS1 | growth arrest-specific 1 |
| 29 | 11.45 | 0.000237 | | |
| 30 | 11.39 | 0.000207 | CXCL16 | chemokine (C—X—C motif) ligand 16; NULL |
| 31 | 10.87 | 0.00025 | PITPNC1 | phosphatidylinositol transfer protein, cytoplasmic 1 |
| 32 | 10.6 | 0.000128 | NR4A2 | nuclear receptor subfamily 4, group A, member 2 |
| 33 | 10.56 | 0.000062 | FZD8 | frizzled family receptor 8; microRNA 4683 |
| 34 | 10.11 | 0.037241 | MIR3189 | microRNA 3189 |
| 35 | 10.03 | 0.000307 | ADAMTS5 | ADAM metallopeptidase with thrombospondin type 1 motif, 5 |
| 36 | 9.86 | 0.002102 | CXCL1 | chemokine (C—X—C motif) ligand 1 (melanoma growth stimulating activity, alpha) |
| 37 | 9.62 | 0.000104 | LIF | leukemia inhibitory factor |
| 38 | 9.42 | 0.000944 | RAB27B | RAB27B, member RAS oncogene family |
| 39 | 9.39 | 0.000091 | GEM | GTP binding protein overexpressed in skeletal muscle |
| 40 | 9.06 | 0.000311 | | |
| 41 | 9.03 | 0.000797 | HAS1 | hyaluronan synthase 1 |
| 42 | −8.96 | 0.006205 | CTGF | connective tissue growth factor |
| 43 | −9.3 | 0.024107 | KRTAP2-3 | keratin associated protein 2-3; keratin associated protein 2-4 |
| 44 | −9.78 | 0.000051 | TOP2A | topoisomerase (DNA) II alpha 170 kDa |
| 45 | −10.56 | 0.000014 | PBK | PDZ binding kinase |
| 46 | −10.63 | 0.000022 | TPX2 | TPX2, microtubule-associated, homolog (*Xenopus laevis*) |
| 47 | −11.27 | 0.003641 | | |
| 48 | −11.48 | 0.000012 | DLGAP5 | discs, large (*Drosophila*) homolog-associated protein 5 |
| 49 | −12.52 | 0.000018 | CCNA2 | cyclin A2 |
| 50 | −12.72 | 0.002789 | | |
| 51 | −14.5 | 0.000007 | ANLN | anillin, actin binding protein; NULL |
| 52 | −14.75 | 0.002755 | CYR61 | cysteine-rich, angiogenic inducer, 61 |
| 53 | −15.07 | 0.000217 | B3GALT2 | UDP-Gal:betaGlcNAc beta 1,3-galactosyltransferase, polypeptide 2 |
| 54 | −15.21 | 0.001511 | ALPL | alkaline phosphatase, liver/bone/kidney; NULL |
| 55 | −18.93 | 0.000415 | TAGLN | Transgelin |
| 56 | −27.82 | 0.005062 | PTX3 | pentraxin 3, long |

Example 3

Comparison of MSC-NTFs Using Two Different Differentiation Protocols

Materials and Methods

Differentiation protocol 1: As described in Example 1—this is referred to herein as the one-step protocol.

Differentiation protocol 2: As described in WO2009/144718—this is referred to herein as the two-step protocol.

In short, human MSC (12,000 cells/cm$^2$) were first placed in DMEM supplemented with SPN, 2 mM L-Glutamine (Biological industries), 20 ng/ml human epidermal growth factor (hEGF), 20 ng/ml human basic fibroblast growth factor (hbFGF) (R&D Systems) and N2 supplement (Invitrogen). After 72 hours, the medium was replaced with DMEM supplemented with 1 mM dibutyryl cyclic AMP (dbcAMP), 0.5 mM isobutylmethylxanthine (IBMX) (Sigma-Aldrich), 5 ng/ml human platelet derived growth factor (PDGF), 50 ng/ml human neuregulin 1-β1/HRG1-β1 EGF domain and 20 ng/ml hbFGF (all from R&D Systems) for 3 more days.

Proteomics: Performed as described in Example 2.

Gene Array Analyses: Performed as described in Example 2.

The experiment compared MSC-NTF cells induced to differentiate by the one step protocol or by the two step protocol. Samples from three unrelated subjects were analyzed for each condition. The overall difference between individuals was found to be smaller than between conditions. The overall difference between each differentiation protocol and the control was found to be greater than between the protocols.

Results

The most significantly up- or down-regulated proteins identified when comparing MSC cells differentiated by the two protocols, based on identification by at least two peptides in three repeats using Mass spec, normalized for the intensity of the detection of the protein are presented in Table 4, herein below.

TABLE 4

| | Protein ID | Majority Protein ID | Protein Name | Gene name | Welch P Value | Welch difference |
|---|---|---|---|---|---|---|
| 1 | Q9BVA1 | Q9BVA1 | Tubulin beta-2B chain | TUBB2B | 0.000583 | 3.441701 |
| 2 | Q15392; H7C4B7 | Q15392 | Delta(24)-sterol reductase | DHCR24 | 0.013112 | −3.09319 |
| 3 | S4R371; P05413; S4R3A2 | S4R371; P05413; S4R3A2 | Fatty acid-binding protein, heart | FABP3 | 0.03411 | −3.10571 |
| 4 | E7EVP7; Q14643; B7ZMI3 | E7EVP7; Q14643 | Inositol 1,4,5-trisphosphate receptor type 1 | ITPR1 | 0.00456 | −3.58643 |
| 5 | O95757; E9PDE8; D6RJ96 | O95757; E9PDE8; D6RJ96 | Heat shock 70 kDa protein 4L | HSPA4L | 0.040802 | −3.66797 |
| 6 | G5E9F5; B5MC53; B5MCF8; P39210; C9J473; H0Y6M5; E7EX18 | G5E9F5; B5MC53; B5MCF8; P39210; C9J473; H0Y6M5; E7EX18 | Protein Mpv17 | MPV17 | 0.002826 | −6.1913 |
| 7 | Q8N2G8; K7ESN3 | Q8N2G8; K7ESN3 | GH3 domain-containing protein | GHDC | 0.000996 | −3.30843 |
| 8 | P08236; F8WBK6; F2Z3L6 | P08236 | Beta-glucuronidase | GUSB | 0.014338 | −3.70965 |
| 9 | H3BUL4; H3BMX9; Q9GZU8; H3BQQ6; H3BTI2; H3BTP8; H3BSY6; H3BP64; H3BU93; Q6P4H7; H3BSF0; H3BNK9 | H3BUL4; H3BMX9; Q9GZU8; H3BQQ6; H3BTI2; H3BTP8; H3BSY6; H3BP64; H3BU93 | Protein FAM192A | FAM192A | 0.022477 | 3.316088 |

Out of a total of 48,226 genes that were analyzed, 100 genes were found to be up-regulated in the two step protocol as compared to the one step protocol and 69 genes were found to be down-regulated in the two step protocol as compared to the one step protocol.

Table 5, herein below provides a list of exemplary genes that were significantly up or down regulated following differentiation.

TABLE 5

| | Transcript Cluster ID | Protocol2 Bi-weight Avg Signal (log2) | Protocol1 Bi-weight Avg Signal (log2) | Fold Change (linear) (Protocol2 vs. Protocol1) | ANOVA p-value (Protocol2 vs. Protocol1) | FDR p-value (Protocol2 vs. Protocol1) | Gene Symbol |
|---|---|---|---|---|---|---|---|
| 1 | 16913537 | 9.31 | 6.4 | 7.54 | 0.002082 | 0.394067 | LBP |
| 2 | 17080516 | 11.59 | 8.91 | 6.44 | 0.000435 | 0.26432 | ENPP2 |
| 3 | 16908197 | 11.76 | 9.29 | 5.51 | 0.00794 | 0.474763 | IGFBP5 |
| 4 | 16919242 | 10.33 | 7.91 | 5.34 | 0.004 | 0.439362 | MAFB |
| 5 | 17075789 | 8 | 5.74 | 4.77 | 0.000235 | 0.227658 | SCARA5 |

TABLE 5-continued

| | Transcript Cluster ID | Protocol2 Bi-weight Avg Signal (log2) | Protocol1 Bi-weight Avg Signal (log2) | Fold Change (linear) (Protocol2 vs. Protocol1) | ANOVA p-value (Protocol2 vs. Protocol1) | FDR p-value (Protocol2 vs. Protocol1) | Gene Symbol |
|---|---|---|---|---|---|---|---|
| 6 | 16716371 | 10.36 | 8.2 | 4.49 | 0.004162 | 0.440384 | CH25H |
| 7 | 16691327 | 7.75 | 5.67 | 4.23 | 0.004869 | 0.444802 | NGF |
| 8 | 16816034 | 11.72 | 9.65 | 4.21 | 0.00035 | 0.263671 | NPIPA1 |
| 9 | 16795943 | 6.39 | 4.34 | 4.13 | 0.005322 | 0.450478 | TC2N |
| 10 | 16944010 | 9.12 | 7.14 | 3.93 | 0.00011 | 0.198375 | BOC |
| 11 | 16782003 | 6.6 | 4.62 | 3.93 | 0.01791 | 0.583076 | TRDV3 |
| 12 | 16863593 | 6.96 | 5.04 | 3.8 | 0.000775 | 0.319307 | C5AR2 |
| 13 | 16816287 | 11.37 | 9.47 | 3.73 | 0.000126 | 0.198375 | PKD1P1 |
| 14 | 16824400 | 11.84 | 9.95 | 3.7 | 0.000078 | 0.198375 | NPIPA5 |
| 15 | 16676988 | 8.61 | 6.73 | 3.68 | 0.018038 | 0.583776 | HSD11B1 |
| 16 | 16853879 | 6.92 | 5.09 | 3.56 | 0.017063 | 0.575446 | PIEZO2 |
| 17 | 16774384 | 10.24 | 8.44 | 3.49 | 0.001238 | 0.353527 | TNFSF11 |
| 18 | 16888669 | 4.22 | 2.42 | 3.46 | 0.009271 | 0.497877 | MIR1245A |
| 19 | 16980762 | 8.43 | 6.68 | 3.37 | 0.001297 | 0.353527 | SFRP2 |
| 20 | 16730967 | 8.12 | 6.37 | 3.37 | 0.001278 | 0.353527 | C11orf87 |
| 21 | 16814986 | 8.63 | 6.91 | 3.29 | 0.049553 | 0.722228 | MIR4516 |
| 22 | 16824127 | 9.21 | 7.53 | 3.2 | 0.004523 | 0.440937 | LOC100288162 |
| 23 | 16729290 | 11.15 | 9.5 | 3.15 | 0.000002 | 0.02648 | TSKU |
| 24 | 16936947 | 8.33 | 6.69 | 3.12 | 0.029614 | 0.660051 | ITPR1 |
| 25 | 16840113 | 10.27 | 8.65 | 3.07 | 0.030963 | 0.664666 | CXCL16 |
| 26 | 16742384 | 7.95 | 6.34 | 3.04 | 0.00703 | 0.472433 | LRRC32 |
| 27 | 16824366 | 11.58 | 9.97 | 3.03 | 0.000113 | 0.198375 | PKD1P1 |
| 28 | 16996234 | 9.47 | 7.89 | 3 | 0.003441 | 0.414166 | PPAP2A |
| 29 | 16824193 | 12.35 | 10.81 | 2.9 | 0.000085 | 0.198375 | NPIPA5 |
| 30 | 16774427 | 11.1 | 9.59 | 2.83 | 0.03554 | 0.675853 | LACC1 |
| 31 | 16774303 | 5.41 | 3.92 | 2.81 | 0.013365 | 0.537579 | RGCC |
| 32 | 16994002 | 8.38 | 6.92 | 2.75 | 0.000489 | 0.275839 | LPCAT1 |
| 33 | 16756447 | 6.35 | 4.91 | 2.71 | 0.004243 | 0.440384 | BTBD11 |
| 34 | 17043843 | 8.43 | 6.99 | 2.71 | 0.032515 | 0.666018 | TSPAN13 |
| 35 | 17087109 | 6.24 | 4.82 | 2.68 | 0.009133 | 0.497794 | MIR27B |
| 36 | 16970435 | 8.54 | 7.14 | 2.65 | 0.003122 | 0.410198 | SPRY1 |
| 37 | 16816343 | 12.62 | 11.21 | 2.65 | 0.000222 | 0.227658 | NPIPA1 |
| 38 | 16910070 | 7.35 | 5.95 | 2.64 | 0.016769 | 0.571533 | MIR4441 |
| 39 | 16723020 | 6.53 | 5.14 | 2.62 | 0.003207 | 0.413056 | ANO3 |
| 40 | 16825484 | 10.52 | 9.2 | 2.5 | 0.003972 | 0.438334 | NPIPB3 |
| 41 | 16746930 | 9.68 | 8.36 | 2.49 | 0.005319 | 0.450478 | TSPAN9 |
| 42 | 16893349 | 10.77 | 9.46 | 2.48 | 0.009614 | 0.504379 | SNED1 |
| 43 | 16824166 | 9.15 | 7.86 | 2.44 | 0.00181 | 0.383976 | LOC399491 |
| 44 | 16871235 | 7.62 | 6.34 | 2.43 | 7.56E−07 | 0.02648 | CEBPA |
| 45 | 17088462 | 11.37 | 10.11 | 2.41 | 0.005785 | 0.456611 | PAPPA |
| 46 | 16890675 | 7.61 | 6.34 | 2.41 | 0.012505 | 0.529023 | IGFBP2 |
| 47 | 16920047 | 9.28 | 8.03 | 2.39 | 0.003573 | 0.414166 | PREX1 |
| 48 | 17005077 | 8.19 | 6.95 | 2.36 | 0.01056 | 0.508075 | MYLIP |
| 49 | 16824349 | 8.83 | 7.59 | 2.36 | 0.000113 | 0.198375 | LOC100288162 |
| 50 | 16661646 | 10.07 | 8.84 | 2.35 | 0.005955 | 0.457174 | RNU11 |
| 51 | 16976827 | 11.73 | 10.5 | 2.34 | 0.036147 | 0.67781 | CXCL5 |
| 52 | 16970465 | 7.83 | 6.61 | 2.34 | 0.004538 | 0.440937 | FAT4 |
| 53 | 16661730 | 10.28 | 9.06 | 2.33 | 0.016407 | 0.567596 | PTPRU |
| 54 | 16990203 | 6.9 | 5.69 | 2.32 | 0.04901 | 0.722228 | VTRNA1-3 |
| 55 | 16795965 | 8.98 | 7.77 | 2.31 | 0.003339 | 0.414166 | FBLN5 |
| 56 | 17012140 | 5.05 | 3.86 | 2.29 | 0.048905 | 0.722228 | RNA5SP215 |
| 57 | 16886174 | 7.46 | 6.27 | 2.28 | 0.017839 | 0.582777 | KYNU |
| 58 | 16802497 | 7.05 | 5.86 | 2.28 | 0.005396 | 0.450478 | PAQR5 |
| 59 | 17023799 | 9.17 | 8.01 | 2.24 | 0.025425 | 0.640796 | SLC2A12 |
| 60 | 16998059 | 10.49 | 9.34 | 2.22 | 0.009737 | 0.506539 | ARRDC3 |
| 61 | 16824352 | 9.6 | 8.45 | 2.22 | 0.000123 | 0.198375 | XYLT1 |
| 62 | 16687875 | 10.61 | 9.46 | 2.21 | 0.045004 | 0.714357 | JUN |
| 63 | 16709072 | 9.48 | 8.35 | 2.19 | 0.002215 | 0.397731 | ADD3 |
| 64 | 16906419 | 6.73 | 5.61 | 2.18 | 0.028857 | 0.658607 | SLC40A1 |
| 65 | 17092081 | 7.91 | 6.79 | 2.17 | 0.004207 | 0.440384 | GLIS3 |
| 66 | 17114272 | 8 | 6.89 | 2.17 | 0.000034 | 0.198375 | GPC4 |
| 67 | 17106688 | 8.03 | 6.92 | 2.16 | 0.003064 | 0.406417 | GRIA3 |
| 68 | 17074029 | 7.38 | 6.27 | 2.15 | 0.010791 | 0.508075 | TDRP |
| 69 | 16754397 | 6.29 | 5.18 | 2.15 | 0.004317 | 0.440384 | LOC652993 |
| 70 | 16689546 | 8.07 | 6.97 | 2.15 | 0.002184 | 0.396235 | TGFBR3 |
| 71 | 16997010 | 6.03 | 4.94 | 2.13 | 0.017556 | 0.58068 | OTTHUMG00000163317 |
| 72 | 17004989 | 7.05 | 5.97 | 2.12 | 0.001592 | 0.376991 | RNF182 |
| 73 | 16923766 | 8.31 | 7.25 | 2.08 | 0.003201 | 0.413056 | COL18A1 |
| 74 | 16832350 | 9.58 | 8.54 | 2.07 | 0.000392 | 0.263671 | KSR1 |
| 75 | 16781511 | 5.34 | 4.29 | 2.07 | 0.011554 | 0.517382 | RNA5SP382 |
| 76 | 17020258 | 5.01 | 3.97 | 2.06 | 0.046083 | 0.717241 | BMP5 |
| 77 | 16687737 | 10.22 | 9.18 | 2.05 | 0.042364 | 0.702396 | PPAP2B |
| 78 | 16995989 | 5.96 | 4.92 | 2.04 | 0.002448 | 0.404044 | FGF10 |
| 79 | 17101292 | 8.17 | 7.14 | 2.04 | 0.010667 | 0.508075 | STS |
| 80 | 16696295 | 9.41 | 8.39 | 2.03 | 0.000133 | 0.198375 | KIFAP3 |

TABLE 5-continued

| | Transcript Cluster ID | Protocol2 Bi-weight Avg Signal (log2) | Protocol1 Bi-weight Avg Signal (log2) | Fold Change (linear) (Protocol2 vs. Protocol1) | ANOVA p-value (Protocol2 vs. Protocol1) | FDR p-value (Protocol2 vs. Protocol1) | Gene Symbol |
|---|---|---|---|---|---|---|---|
| 81 | 16915530 | 4.49 | 3.46 | 2.03 | 0.034023 | 0.672731 | MIR548AG2 |
| 82 | 16665588 | 7.06 | 6.05 | 2.02 | 0.042012 | 0.702396 | ROR1 |
| 83 | 16949759 | 8.52 | 9.52 | −2.01 | 0.000136 | 0.198375 | HES1 |
| 84 | 16836021 | 6.04 | 7.06 | −2.03 | 0.010652 | 0.508075 | ABCC3 |
| 85 | 16904324 | 10.66 | 11.68 | −2.03 | 0.006644 | 0.469744 | FAP |
| 86 | 16743707 | 4.44 | 5.47 | −2.04 | 0.010679 | 0.508075 | MMP10 |
| 87 | 17059119 | 9.28 | 10.33 | −2.06 | 0.028998 | 0.659121 | SEMA3C |
| 88 | 16885290 | 6.34 | 7.38 | −2.06 | 0.000553 | 0.285095 | GYPC |
| 89 | 17084025 | 5.26 | 6.32 | −2.09 | 0.047689 | 0.719821 | FLJ35282 |
| 90 | 17003640 | 7.3 | 8.36 | −2.09 | 0.001358 | 0.35533 | ADAMTS2 |
| 91 | 16972229 | 5.13 | 6.23 | −2.15 | 0.023153 | 0.625718 | ANXA10 |
| 92 | 17072601 | 6.53 | 7.64 | −2.16 | 0.003707 | 0.421757 | TRIB1 |
| 93 | 17024746 | 7.11 | 8.23 | −2.17 | 0.002144 | 0.396226 | ZBTB2 |
| 94 | 16712292 | 5.73 | 6.88 | −2.22 | 0.002665 | 0.404044 | PTPLA |
| 95 | 16894710 | 6.38 | 7.56 | −2.27 | 0.01071 | 0.508075 | FAM49A |
| 96 | 16856803 | 6.72 | 7.95 | −2.35 | 0.011267 | 0.514555 | GADD45B |
| 97 | 16738630 | 6.53 | 7.76 | −2.35 | 0.000374 | 0.263671 | LPXN |
| 98 | 16927633 | 7.48 | 8.73 | −2.39 | 0.018384 | 0.586973 | SDF2L1 |
| 99 | 16818359 | 7.66 | 8.91 | −2.39 | 0.002451 | 0.404044 | TGFB1I1 |
| 100 | 16851486 | 6.43 | 7.73 | −2.46 | 0.007203 | 0.472433 | LAMA3 |
| 101 | 16843162 | 6 | 7.3 | −2.47 | 0.006176 | 0.462493 | EVI2B |
| 102 | 17063221 | 6.44 | 7.75 | −2.48 | 0.001754 | 0.383976 | FAM180A |
| 103 | 16886717 | 9.72 | 11.04 | −2.5 | 0.01795 | 0.583334 | GALNT5 |
| 104 | 16677451 | 6.04 | 7.39 | −2.55 | 0.003262 | 0.413056 | KCNK2 |
| 105 | 17049904 | 4.79 | 6.15 | −2.58 | 0.02116 | 0.609685 | LRRC17 |
| 106 | 16691090 | 5.86 | 7.27 | −2.66 | 0.014476 | 0.552858 | PTPN22 |
| 1-7 | 16819325 | 9.52 | 10.94 | −2.68 | 0.007272 | 0.472433 | HERPUD1 |
| 108 | 17020846 | 8.51 | 9.95 | −2.73 | 0.02339 | 0.627571 | COL12A1 |
| 109 | 16932483 | 4.38 | 5.84 | −2.75 | 0.010589 | 0.508075 | OTTHUMG00000150605 |
| 110 | 16749583 | 5.53 | 7 | −2.77 | 0.01259 | 0.53004 | FAR2 |
| 111 | 17072920 | 8.18 | 9.65 | −2.77 | 0.007433 | 0.472433 | WISP1 |
| 112 | 16843167 | 4.15 | 5.65 | −2.84 | 0.016867 | 0.573091 | EVI2A |
| 113 | 16858137 | 7.64 | 9.14 | −2.84 | 0.047828 | 0.720122 | ICAM1 |
| 114 | | | | | | | |
| 115 | 16853716 | 6.51 | 8.04 | −2.89 | 0.001064 | 0.346851 | LAMA1 |
| 116 | 16901974 | 4.82 | 6.41 | −3 | 0.045208 | 0.715302 | IL1A |
| 117 | 16901986 | 5.88 | 7.47 | −3.01 | 0.013368 | 0.537579 | IL1B |
| 118 | 16665558 | 4.21 | 5.84 | −3.09 | 0.00274 | 0.404044 | DLEU2L |
| 119 | 16762661 | 7.5 | 9.16 | −3.16 | 0.003526 | 0.414166 | PTHLH |
| 120 | 16773681 | 9.66 | 11.32 | −3.17 | 0.038394 | 0.686809 | MEDAG |
| 121 | 17046135 | 8.55 | 10.22 | −3.19 | 0.001125 | 0.35235 | EGFR |
| 122 | 16766578 | 5.47 | 7.17 | −3.24 | 0.016333 | 0.565871 | DDIT3 |
| 123 | 16761212 | 6.09 | 7.82 | −3.31 | 0.003101 | 0.408572 | CLEC2B |
| 124 | 16743148 | 5.08 | 7.05 | −3.92 | 0.007367 | 0.472433 | NOX4 |
| 125 | 16903919 | 5.02 | 7.05 | −4.09 | 0.025013 | 0.63692 | ERMN |
| 126 | 16743721 | 6.09 | 8.85 | −6.77 | 0.007019 | 0.472433 | MMP1 |

Example 4

Immunomodulation Effects of MSC and MSC-NTF

Mesenchymal stem cells (MSCs) have been shown to have considerable immunomodulatory activities. They are currently being tested in clinical trials for the treatment of various diseases owing to their immunosuppressive properties.

The immunomodulatory properties of MSC and MSC-NTF were compared using in-vitro assays measuring their effect on T-cells activation by determining the number of CD4 positive cells and by T-cell cytokine production using ELISA assays.

Materials and Methods

Peripheral blood mono-nuclear cells (PBMC) were isolated from fresh peripheral blood of healthy volunteers by Ficoll density centrifugation.

MSC-NTF cells were induced to differentiate using the one step protocol described in Example 1. PBMC were co-cultured with either MSC or with MSC-NTF cells in 12-well plates in culture medium containing RPMI and 10% FBS. PBMC were activated using PHA 10 μg/ml. Activated PBMC were cultured alone or co-cultured with either MSC or MSC-NTF cells.

After 4 days of co-culture, the non-adherent PBMC were harvested by gentle pipetting and the culture supernatant was collected for cytokine analysis (IL-10, and IFN-γ) by ELISA.

The non-adherent PBMCs were analyzed by flow-cytometry for the levels of CD4 positive T-cells.

Results

The results are summarized in Table 6 herein below.

TABLE 6

| Cell type | INF-γ (pg/ml) | IL-10 (pg/ml) | CD4 (% positives) |
|---|---|---|---|
| Non-activated PBMC | 0.0 | 0.0 | |
| Activated PBMC | 765.8 | 2016.9 | 26.4 |
| Activated PBMC + MSC | 80.41 | 953.6 | 16.58 |
| Activated PBMC + MSC-NTF | 9.1 | 602.8 | 13.8 |
| MSC | 0.0 | 0.0 | |
| MSC-NTF | 0.0 | 0.0 | |

These results confirm the immunomodulatory effect of MSC-NTF cells and further demonstrate that such an effect is enhanced as compared to non-differentiated MSCs of the same donor. Interferon-gamma and IL-10 secretion by activated PBMC are significantly downregulated by the MSC-NTF cells by 85 and 3.3 fold respectively. Neither MSC nor MSC-NTF cells alone were found to secrete either Interferon-gamma or IL-10.

In addition, MSC-NTF cells led to a reduction of CD4 positive cells to half their number in the control culture in the absence of MSC-NTF cells (from 26.4 to 13.8%).

Example 5

Stability of MSC-NTF

To evaluate post-harvest stability of MSC-NTF cells, freshly harvested MSC-NTF cells (the population having been analyzed to ensure that more than 80% of the cells thereof expressed CD49a) were re-suspended in culture medium, packed in syringes used for administration to patients and incubated at 2-8° C. for up to 4 days. At 24, 48, 72 and 96 hour time points, cells were sampled and counted and viable cell concentration and viability were assessed. At each time point the cells were also reseeded and cultured for three additional days in culture medium at 37° C. to evaluate Delayed Onset Cell Death. Recovery of viable cells and viability was established at each time point.

Results

Viability and viable MSC-NTF cell concentration was shown to be maintained for up to 96 hours when packed in syringes as used for administration to patients in clinical trials. Viable cell concentration was practically unchanged for the first 72 hours and only decreased to about 96% of time 0 after 96 hours in the syringes (FIG. 3A). Furthermore incubation of cells for three additional days to evaluate Delayed Onset Cell Death confirmed that the cells maintain stability and viability for at least 72 hours. At 96 hours there is a decline to 86% of the number of viable cells recovered (FIG. 3B). Based on the recovery of viable cells in the syringes and following 3 days in culture, it appears that cell stability is maintained for up to 96 hours. Cells were shown to maintain their characteristic phenotype and neurotrophic factor secretion properties throughout the 96 hours stability period.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A pharmaceutical composition comprising a culture medium as a carrier and an isolated population of differentiated human bone marrow-derived mesenchymal stem cells (MSCs) that secrete neurotrophic factors, wherein at least 80% of said differentiated human bone marrow-derived MSCs express cell surface marker CD49a, wherein said population of differentiated MSCs are ex vivo generated by differentiating a population of undifferentiated MSCs of a subject in a single differentiating medium comprising basic fibroblast growth factor (bFGF), platelet derived growth factor (PDGF), heregulin and cAMP for at least two days, wherein more than 95% of the cells of said population of undifferentiated MSCs express CD73, CD90 and CD105 and lack expression of CD3, CD14, CD19, CD34, CD45, and HLA-DR as determined by flow cytometry, wherein said differentiating is carried out in a single step and wherein said carrier preserves the number of cells in the composition for at least 24 hours.

2. The pharmaceutical composition of claim 1, wherein at least 90% of the cells of the population express CD49a.

3. The pharmaceutical composition of claim 1, wherein said differentiating medium is devoid of isobutylmethylxanthine (IBMX).

4. The pharmaceutical composition of claim 1, wherein said neurotrophic factors are selected from the group consisting of GDNF, VEGF and HGF.

5. The pharmaceutical composition of claim 1, wherein said culture medium is DMEM.

* * * * *